United States Patent
Wurtz et al.

(10) Patent No.: US 12,281,108 B2
(45) Date of Patent: Apr. 22, 2025

(54) PYRROLIDINONE DERIVATIVES AS FORMYL PEPTIDE 2 RECEPTOR AGONISTS

(71) Applicant: BRISTOL-MYERS SQUIBB COMPANY, Princeton, NJ (US)

(72) Inventors: Nicholas R. Wurtz, Pennington, NJ (US); James A. Johnson, Pennington, NJ (US); Zulan Pi, Pennington, NJ (US); Andrew Quoc Viet, Schwenksville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 948 days.

(21) Appl. No.: 17/295,092

(22) PCT Filed: Nov. 25, 2019

(86) PCT No.: PCT/US2019/062905
§ 371 (c)(1),
(2) Date: May 19, 2021

(87) PCT Pub. No.: WO2020/112583
PCT Pub. Date: Jun. 4, 2020

(65) Prior Publication Data
US 2022/0002281 A1    Jan. 6, 2022

Related U.S. Application Data

(60) Provisional application No. 62/819,832, filed on Mar. 18, 2019, provisional application No. 62/771,196, filed on Nov. 26, 2018.

(51) Int. Cl.
| | |
|---|---|
| C07D 413/14 | (2006.01) |
| C07D 413/12 | (2006.01) |
| C07D 417/12 | (2006.01) |
| C07D 417/14 | (2006.01) |
| C07D 498/04 | (2006.01) |
| A61K 31/423 | (2006.01) |
| A61K 31/4245 | (2006.01) |
| A61K 31/433 | (2006.01) |
| A61P 9/04 | (2006.01) |
| A61P 9/10 | (2006.01) |
| A61P 11/00 | (2006.01) |

(52) U.S. Cl.
CPC ......... C07D 413/14 (2013.01); C07D 413/12 (2013.01); C07D 417/12 (2013.01); C07D 417/14 (2013.01); C07D 498/04 (2013.01)

(58) Field of Classification Search
CPC .. C07D 413/14; C07D 413/12; C07D 417/12; C07D 417/14; C07D 498/04; A61P 9/04; A61P 9/10; A61P 11/00; A61K 31/423; A61K 31/4245; A61K 31/433
See application file for complete search history.

(56) References Cited

U.S. PATENT DOCUMENTS

| | | | |
|---|---|---|---|
| 9,822,069 B2 * | 11/2017 | Takahashi et al. | |
| 10,029,983 B2 | 7/2018 | Takahashi et al. | |
| 10,252,992 B2 | 4/2019 | Takahashi et al. | |
| 10,464,891 B2 | 11/2019 | Takahashi et al. | |
| 11,767,291 B2 * | 9/2023 | Kattamuri ............ | C07D 307/79 |
| | | | 564/84 |

FOREIGN PATENT DOCUMENTS

| | | |
|---|---|---|
| WO | 2016189876 A1 | 12/2016 |
| WO | 2016189877 A1 | 12/2016 |
| WO | 2017091496 A1 | 6/2017 |
| WO | 2017100390 A1 | 6/2017 |
| WO | 2018054549 A1 | 3/2018 |
| WO | 2018227058 A9 | 12/2018 |
| WO | 2018227061 A1 | 12/2018 |
| WO | 2018227065 A1 | 12/2018 |
| WO | 2018227067 A1 | 12/2018 |
| WO | 2019173182 A1 | 9/2019 |
| WO | 2020257161 A1 | 12/2020 |

OTHER PUBLICATIONS

Corminboeuf.et al., (J. Med. Chem. vol. 58, 2, 537-559, 2014., FPR2/ALXR Agonists and the Resolution of Inflammation (Year: 2014).*

Boström J, Hogner A, Llinàs A, Wellner E, Plowright AT. Oxadiazoles in medicinal chemistry. J Med Chem. Mar. 8, 2012;55(5):1817-30. doi: 10.1021/jm2013248. Epub Jan. 13, 2012. PMID: 22185670. (Year: 2012).*

Cattaneo et al., "Distinct Signaling Cascades Elicited by Different Formyl Peptide Receptor 2 (FPR2) Agonists" Int. J. Mol. Sci., vol. 14, pp. 7193-7230 (2013).

Chandrasekharan et al., "Lipoxins: nature's way to resolve inflammation", Journal of Inflammation Research, 2015:8 181-192.

(Continued)

*Primary Examiner* — Bruck Kifle
*Assistant Examiner* — Kevin S Martin
(74) *Attorney, Agent, or Firm* — Hong Liu

(57) ABSTRACT

The disclosure relates to compounds of formula (I), which are formyl peptide 2 (FPR2) receptor agonists and/or formyl peptide 1 (FPR1) receptor agonists. The disclosure also provides compositions and methods of using the compounds, for example, for the treatment of atherosclerosis, heart failure, and related diseases.

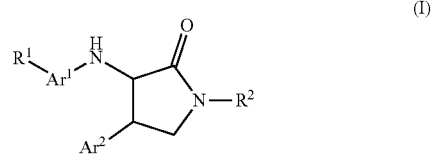

(I)

7 Claims, No Drawings

(56) References Cited

OTHER PUBLICATIONS

Chen et al., "Regulation of inflammation by members of the formyl-peptide receptor family", Journal of Autoimmunity vol. 85, pp. 64-77 (2017).
Corminboeuf, et al. "FPR2/ALXR Agonists and the Resolution of Inflammation", J. Med. Chem. 2015, 58, 537-559.
Fredman et al., "Targeted nanoparticles containing the proresolvingpeptide Ac2-26 protect against advancedatherosclerosis in hypercholesterolemic mice", Sci. Trans. Med., 2015, 7(275); pp. 275ra20).
Gavins, Felicity N.E., "Are formyl peptide receptors novel targets for therapeutic intervention ischaemia-reperfusion injury?" Trends in Pharmacological Sciences, vol. 31(6), pp. 266-276 (2010).
Kain et al., "Resolvin D1 activates the inflammation resolving response at splenic and ventricular site following myocardial infarction leading to improved ventricular function", Journal of Molecular and Cellular Cardiology, vol. 84, pp. 24-35 (2015).
Liu et al., "Lipoxin A4 ameliorates ischemia/reperfusion induced spinal cord injury in rabbit model", Int. J. Clin.Exp. Medicine, Vo. 8(8), pp. 12826-12833 (2015.
Perretti, et al., "Resolution Pharmacology: Opportunities for Therapeutic Innovationin Inflammation", Trends in Pharmacological Sciences, vol. 36(11) 2015.
Petri et al., "The role of the FPR2/ALX receptor in atherosclerosis development and plaque stability", Cardiovascular Research, vol. 105, pp. 65-74 (2015).
Romano et al., "Lipoxins and aspirin-triggered lipoxinsin resolution of inflammation", European Journal of Pharmacology vol. 760 pp. 49-63 (2015).
Tsai et al., "Formyl peptide receptor modulators: a patent review and potential applications for inflammatory diseases" Expert Opinion on Therapeutic Patents, vol. 26, No. 10, 1139-1156 (2016).
Ye et al., "International Union of Basic and Clinical Pharmacology. LXXIII. Nomenclature for the Formyl Peptide Receptor (FPR) Family", Pharmacological Reviews, vol. 61(2), 2009.

* cited by examiner

PYRROLIDINONE DERIVATIVES AS FORMYL PEPTIDE 2 RECEPTOR AGONISTS

CROSS REFERENCE TO RELATED APPLICATIONS

This application is a 371 application of PCT/US2019/062905, filed Nov. 25, 2019, which is entitled to priority pursuant to 35 U.S.C. § 119(e) to U.S. provisional patent application No. 62/771,196, filed Nov. 26, 2018 and U.S. provisional application No. 62/819,832, filed Mar. 18, 2019, which are incorporated herein in their entirety.

BACKGROUND OF THE INVENTION

The present invention relates to novel pyrrolidinone compounds of formula I which are formyl peptide 2 (FPR2) receptor agonists, and also relates to compositions containing them, and methods of using them, for example, for the treatment of atherosclerosis, heart failure, chronic obstructive pulmonary disease (COPD), and related diseases.

Formyl peptide receptor 2 (FPR2) belongs to a small group of seven-transmembrane domain, G protein-coupled receptors that are expressed in multiple human tissues including immune cells and are known to be important in host defense and inflammation. FPR2 shares significant sequence homology with FPR1 and FPR3 (Journal of Autoimmunity 85, 2017, 64-77). Collectively, these receptors bind a number of structurally diverse agonists, including N-formyl and non-formyl peptides which act as chemo attractants and activate phagocytes. The endogenous peptide Annexin A1 and its N-terminal fragments are examples of ligands that bind human FPR1 and FPR2. Fatty acids such as the eicosanoid lipoxin A4, which belongs to a class of small pro-resolution mediators (SPMs), has also been reported as an agonist for FPR2 (Ye R D., et al., Pharmacol. Rev., 2009, 61, 119-61).

Endogenous FPR2 pro-resolution ligands, such as lipoxin A4 and Annexin A1, have been reported to trigger a wide array of cytoplasmatic cascades such as Gi coupling, $Ca^{2+}$ mobilization and β-arrestin recruitment. (Int J Mol Sci. 2013 April; 14(4): 7193-7230). FPR2 regulates both innate and adaptive immune systems including neutrophils, macrophages, T-, and B-cells. In neutrophils, FPR2 ligands modulate movement, cytotoxicity and life span. In macrophages, agonism of FPR2 prevents apoptosis and enhances efferocytosis. (Chandrasekharan J A, Sharma-Walia N., J. Inflamm. Res., 2015, 8, 181-92). The initiation of resolution of inflammation by FPR2 agonism is responsible for enhancing anti-fibrotic wound healing and returning of the injured tissue to homeostasis (Romano M., et al., Eur. J. Pharmacol., 2015, 5, 49-63).

Chronic inflammation is part of the pathway of pathogenesis of many human diseases and stimulation of resolution pathways with FPR2 agonists may have both protective and reparative effects. Ischemia-reperfusion (I/R) injury is a common feature of several diseases associated with high morbidity and mortality, such as myocardial infarction and stroke. Non-productive wound healing associated with cardiomyocyte death and pathological remodeling resulting from ischemia-reperfusion injury leads to scar formation, fibrosis, and progressive loss of heart function. FPR2 modulation is proposed to enhance myocardial wound healing post injury and diminish adverse myocardial remodeling (Kain V., et al., J. Mol. Cell. Cardiol., 2015, 84, 24-35). In addition, FPR2 pro-resolution agonists, in the central nervous system, may be useful therapeutics for the treatment of a variety of clinical FR conditions, including stroke in brain (Gavins F N., Trends Pharmacol. Sci., 2010, 31, 266-76) and FR induced spinal cord injury (Liu Z Q., et al., Int. J. Clin. Exp. Med., 2015, 8, 12826-33).

In addition to beneficial effects of targeting the FPR2 receptor with novel pro-resolution agonists for treatment of FR induced injury, utility of these ligands can also be applied to other diseases. In the cardiovascular system both the FPR2 receptor and its pro-resolution agonists were found to be responsible for atherogenic-plaque stabilization and healing (Petri M H., et al., Cardiovasc. Res., 2015, 105, 65-74; and Fredman G., et al., Sci. Trans. Med., 2015, 7(275); 275ra20). FPR2 agonists also have been shown to be beneficial in preclinical models of chronic inflammatory human diseases, including: infectious diseases, psoriasis, dermatitis, inflammatory bowel syndrome, Crohn's disease, ocular inflammation, sepsis, pain, metabolic/diabetes diseases, cancer, COPD, asthma and allergic diseases, cystic fibrosis, acute lung injury and fibrosis, rheumatoid arthritis and other joint diseases, Alzheimer's disease, kidney fibrosis, and organ transplantation (Romano M., et al., Eur. J. Pharmacol., 2015, 5, 49-63, Perrett, M., et al., Trends in Pharm. Sci., 2015, 36, 737-755).

DESCRIPTION OF THE INVENTION

The invention encompasses compounds of formula I, which are formyl peptide 2 (FPR2) receptor agonists, compositions containing them, and methods of using them, for example, in the treatment of atherosclerosis, heart failure, chronic obstructive pulmonary disease (COPD), and related diseases.

One aspect of the invention is a compound of formula I

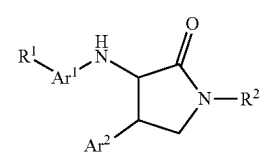

where:

$R^1$ is absent, $Ar^3$, cycloalkyl substituted with 0-2 halo and 0-1 $Ar^4$ substituents, or $((Ar^5)alkyl)(H)NCO$;

$R^2$ is hydrogen, alkyl, or $CH_2CO_2H$;

$Ar^1$ is isoxazolyl, oxadiazolyl, thiadiazolyl, benzoisoxazolyl, isoxazolopyridinyl, or benzooxazolyl, and is substituted with 0-2 halo, alkyl, alkoxy, fluoroalkyl, or fluoroalkoxy substituents;

$Ar^2$ is phenyl, pyridinyl, or pyridazinyl, and is substituted with 1 alkoxy, halo, haloalkyl or haloalkoxy substituent in the 4-position and 0-2 additional halo substituents;

$Ar^3$ is phenyl, pyridinyl, pyridazinyl, pyrimidinyl, or pyrazinyl, and is substituted with 0-3 substituents selected from cyano, halo, alkyl, haloalkyl, cycloalkyl, alkoxy, (cycloalkyl)alkoxy, haloalkoxy, $OAr^6$, alkylthio, haloalkylthio, alkylsulfinyl, haloalkylsulfinyl, and pyrazolyl;

$Ar^4$ is phenyl or pyridinyl substituted with 0-3 substituents selected from cyano, halo, alkyl, haloalkyl, alkoxy, and haloalkoxy;

$Ar^5$ is phenyl or pyridinyl substituted with 0-3 substituents selected from cyano, halo, alkyl, haloalkyl, alkoxy, and haloalkoxy; and Ar⁶ is phenyl, pyridinyl, pyridazinyl, pyrimidinyl, or pyrazinyl, and is substituted with 0-3 substituents selected from cyano, halo, alkyl, haloalkyl, alkoxy, and haloalkoxy;

or a pharmaceutically acceptable salt thereof.

Another aspect of the invention is a compound of formula I where $R^1$ is $Ar^3$; $R^2$ is hydrogen; $Ar^1$ is oxadiazolyl or thiadiazolyl, and is substituted with 0-2 halo, alkyl, alkoxy, fluoroalkyl, or fluoroalkoxy substituents; $Ar^2$ is phenyl substituted with 1 alkoxy, halo, haloalkyl or haloalkoxy substituent in the 4-position and 0-2 additional halo or haloalkyl substituents; $Ar^3$ is phenyl or pyridinyl and is substituted with 0-3 substituents selected from cyano, halo, alkyl, haloalkyl, cycloalkyl, alkoxy, (cycloalkyl)alkoxy, haloalkoxy, $OAr^6$, alkylthio, haloalkylthio, alkylsulfinyl, haloalkylsulfinyl, and pyrazolyl; and $Ar^6$ is phenyl, pyridinyl, pyridazinyl, pyrimidinyl, or pyrazinyl, and is substituted with 0-3 substituents selected from cyano, halo, alkyl, haloalkyl, alkoxy, and haloalkoxy;

or a pharmaceutically acceptable salt thereof.

Another aspect of the invention is a compound of formula I where $R^1$ is $Ar^3$.

Another aspect of the invention is a compound of formula I where $R^2$ is hydrogen.

Another aspect of the invention is a compound of formula I where $Ar^1$ is oxadiazolyl or thiadiazolyl, and is substituted with 0-2 halo, alkyl, alkoxy, fluoroalkyl, or fluoroalkoxy substituents; $Ar^2$ is phenyl substituted with 1 alkoxy, halo, haloalkyl or haloalkoxy substituent in the 4-position and 0-2 additional halo or haloalkyl substituents.

Another aspect of the invention is a compound of formula I where $Ar^3$ is phenyl or pyridinyl and is substituted with 0-3 substituents selected from cyano, halo, alkyl, haloalkyl, cycloalkyl, alkoxy, (cycloalkyl)alkoxy, haloalkoxy, $OAr^6$, alkylthio, haloalkylthio, alkylsulfinyl, haloalkylsulfinyl, and pyrazolyl.

For a compound of Formula I, the scope of any instance of a variable substituent, including $R^1$, $R^2$, $Ar^1$, $Ar^2$, $Ar^3$, $Ar^4$, $Ar^5$, and $Ar^6$ can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Alkoxy" refers to the group "alkyl-O" where "alkyl" is as defined above. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo "Aryl" means a monocyclic or bicyclic aromatic hydrocarbon groups having 6 to 12 carbon atoms, or a bicyclic fused ring system wherein one or both of the rings is aromatic. Bicyclic fused ring systems consist of a phenyl group fused to a four- to seven-membered aromatic or non-aromatic carbocyclic ring. Representative examples of aryl groups include but are not limited to phenyl, indanyl, indenyl, naphthyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms including the structure below with the indicated carbon. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include $^{11}C$, $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

N-formyl peptide receptors (FPRs) are a family of chemo attractant receptors that facilitate leukocyte response during inflammation. FPRs belong to the seven-transmembrane G protein-coupled receptor superfamily and are linked to inhibitory G-proteins (Gi). Three family members (FPR1, FPR2 and FPR3) have been identified in humans and are predominantly found in myeloid cells with varied distribution and have also been reported in multiple organs and tissues. After agonist binding, the FPRs activate a multitude of physiological pathways, such as intra cellular signaling transduction, $Ca^{2+}$ mobilization and transcription. The family interacts with a diverse set of ligands that includes proteins, polypeptides and fatty acid metabolites which activate both pro-inflammatory and pro-resolution downstream responses. FPR2 and FPR1 Cyclic Adenosine Monophosphate (cAMP) Assays were used to measure the in vitro activity of the compounds disclosed in this application.

FPR2 and FPR1 Cyclic Adenosine Monophosphate (cAMP) Assays. A mixture of forskolin (5 µM final for FPR2 or 10 µM final for FPR1) and IBMX (200 µM final) were added to 384-well Proxiplates (Perkin-Elmer) pre-dotted with test compounds in DMSO (1% final) at final concentrations in the range of 0.020 nM to 100 µM. Chinese Hamster Ovary cells (CHO) overexpressing human FPR1 or human FPR2 receptors were cultured in F-12 (Ham's) medium supplemented with 10% qualified FBS, 250 µg/ml zeocin and 300 µg/ml hygromycin (Life Technologies). Reactions were initiated by adding 2,000 human FPR2 cells per well or 4,000 human FPR1 cells per well in Dulbecco's PBS (with calcium and magnesium) (Life Technologies) supplemented with 0.1% BSA (Perkin-Elmer). The reaction mixtures were incubated for 30 min at room temperature. The level of intracellular cAMP was determined using the HTRF HiRange cAMP assay reagent kit (Cisbio) according to manufacturer's instruction. Solutions of cryptate conjugated anti-cAMP and d2 flurorophore-labelled cAMP were made in a supplied lysis buffer separately. Upon completion of the reaction, the cells were lysed with equal volume of the d2-cAMP solution and anti-cAMP solution. After a 1-h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 1 µM to 0.1 pM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The examples disclosed below were tested in the FPR2 and FPR1 cAMP assay described above and found having FPR2 and/or FPR1 agonist activity. A range of $EC_{50}$ values of ≤1 µM (1000 nM) in one of the assays was observed. Table 1 below lists $EC_{50}$ values in the FPR2 and FPR1 cAMP assays measured for the following examples.

TABLE 1

| Example | hFPR2 cAMP2 $EC_{50}$ (uM) | hFPR1 cAMP $EC_{50}$ (uM) |
|---|---|---|
| 18 | 0.0067 | 0.16 |
| 19 | 0.015 | 0.31 |
| 21 | 0.010 | 0.47 |
| 22 | 0.89 | 2.9 |
| 27 | 0.083 | 1.2 |
| 28 | 0.014 | 0.25 |
| 36 | 0.99 | 2.7 |
| 51 | 0.96 | >10 |
| 52 | 0.92 | 0.18 |
| 56 | 0.085 | 0.27 |
| 58 | 0.071 | 0.87 |
| 59 | 0.071 | 0.21 |

The following Examples were tested in the hFPR2 assay described above and found having hFPR2 agonist activity with $EC_{50}$ values of ≤0.040 µM (40 nM): 2, 3, 8, 10, 16, 20, 23, 35, 40, 41, 43, 45, 46, 50, 55, 64, and 68.

The following Examples were tested in the hFPR2 assay described above and found having hFPR2 agonist activity with $EC_{50}$ values between 0.040 µM and 0.150 µM: 7, 12, 17, 29, 30, 31, 32, 34, 42, 44, 48, 49, 53, 57, 60, 65, 66, 61, 62, and 63.

The following Examples were tested in the hFPR2 assay described above and found having hFPR2 agonist activity with $EC_{50}$ values between 0.150 µM and 1.00 µM: 1, 4, 5, 6, 9, 11, 13, 14, 15, 24, 25, 26, 33, 37, 38, 39, 54, and 67.

Pharmaceutical Compositions and Methods of Use

The compounds of the present invention may be administered to mammals, preferably humans, for the treatment of a variety of conditions and disorders including atherosclerosis, heart failure, lung diseases including asthma, COPD, and cystic fibrosis;

neuroinflammatory diseases including multiple sclerosis, Alzheimer's disease, and stroke;

and chronic inflammatory diseases such as inflammatory bowel disease, rheumatoid arthritis, psoriasis, sepsis, and kidney fibrosis.

Unless otherwise specified, the following terms have the stated meanings. The term "subject" refers to any human or other mammalian species that could potentially benefit from treatment with a FPR2 and/or FPR1 agonist as understood by practioners in this field. Some subjects include human beings of any age with risk factors for cardiovascular disease. Common risk factors include age, sex, weight, family history, sleep apnea, alcohol or tobacco use, physical inactivity arrthymia or signs of insulin resistance such as acanthosis nigricans, hypertension, dyslipidemia, or polycystic ovary syndrome (PCOS). The term "patient" means a person suitable for therapy as determined by practitioners in the field. "Treating" or "treatment" cover the treatment of a patient or subject as understood by practitioners in this field. "Preventing" or "prevention" cover the preventive treatment (i.e., prophylaxis and/or risk reduction) of a subclinical disease-state in a patient or subject aimed at reducing the probability of the occurrence of a clinical disease-state as understood by practitioners in this field. Patients are selected for preventative therapy based on factors that are known to increase risk of suffering a clinical disease state compared to the general population. "Therapeutically effective amount" means an amount of a compound that is effective as understood by practitioners in this field.

Another aspect of the invention are pharmaceutical compositions comprising a therapeutically effective amount of a compound of formula I in combination with a pharmaceutical carrier.

Another aspect of the invention are pharmaceutical compositions comprising a therapeutically effective amount of a compound of formula I in combination with at least one other therapeutic agent and a pharmaceutical carrier.

"Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Another aspect of the invention is a method for treating heart disease comprising administering a therapeutically effective amount of a compound of formula I to a patient.

Another aspect of the invention is a method for treating heart disease wherein the heart disease is selected from the group consisting of angina pectoris, unstable angina, myocardial infarction, heart failure, acute coronary disease, acute heart failure, chronic heart failure, and cardiac iatrogenic damage.

Another aspect of the invention is a method for treating heart disease wherein the treatment is post myocardial infarction.

Another aspect of the invention is a method for treating heart disease comprising administering a therapeutically effective amount of a compound of formula I to a patient in conjuction with other therapeutic agents.

The compounds of this invention can be administered by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the invention may be used with at least one of the following heart failure agents selected from loop diuretics, angiotensin converting enzyme (ACE) inhibitors, angiotensin II receptor blockers (ARBs), angiotensin receptor-neprilysin inhibitors (ARNI), beta blockers, mineralocorticoid receptor antagonists, nitroxyl donors, RXFP1 agonists, APJ agonists, SGLT2 inhibitors, HCN potassium-sodium channel inhibitors, myosin modulators, calcium channel inhibitors, chymase inhibitors and cardiotonic agents. These agents include, but are not limited to furosemide, bumetanide, torsemide, sacubitrial-valsartan, thiazide diruetics, captopril, enalapril, lisinopril, carvedilol, metopolol, bisoprolol, serelaxin, spironolactone, eplerenone, ivabradine, candesartan, eprosartan, irbestarain, losartan, olmesartan, telmisartan, and valsartan.

The compounds of the present invention may be employed in combination with at least one of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination at least one of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The compounds of the invention may be used in combination with at least one of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with at least one of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The compounds of the present invention are also useful as standard or reference compounds, for example as a quality standard or control, in tests or assays involving the FPR2. Such compounds may be provided in a commercial kit, for example, for use in pharmaceutical research involving FPR2 activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving FPR2.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries. The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product. The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached. The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Chemistry Methods

The disclosed compounds can be made by various methods known in the art including those of the following schemes and in the specific embodiments section. The structure numbering and variable numbering shown in the synthetic schemes are distinct from and should not be confused with the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, and all changes which come within the meaning and range of equivalency of the claims are therefore intended to be embraced.

A consideration in the planning of any synthetic route in this field is the choice of the protecting group used for protection of the reactive functional groups present in the compounds described in this invention. An authoritative account describing the many alternatives to the trained practitioner is Greene, T. W. et al., Protecting Groups in Organic Synthesis, 4th Edition, Wiley (2007)).

The abbreviations used below are standard organic chemistry abbreviations known by those skilled in this art.

Abbreviations

AcOH or HOAc acetic acid
ACN acetonitrile
ADDP 1,1'-(azodicarbonyl) dipiperidine
$CDCl_3$ deutero-chloroform
$CD_3OD$ deutero-methanol
CDI 1,1'-carbonyldiimidazole
conc concentrated
DCM dichloromethane
DIEA or DIPEA diisopropylethylamine
DMF dimethyl formamide
DMSO dimethyl sulfoxide
DMSO-$d_6$ deutero-dimethyl sulfoxide
$Et_3N$ or TEA triethylamine
EtOAc ethyl acetate
EtOH ethanol
HATU 1-[bis(dimethylamino)methylene]-1H-1,2,3-triazolo[4,5-b]pyridinium 3-oxide hexafluorophosphate
HCl hydrochloric acid
HPLC high-performance liquid chromatography
$K_2HPO_4$ potassium hydrogenphosphate
LCMS liquid chromatography mass spectrometry
MeOH methanol
$MgSO_4$ magnesium sulfate
NMP N-methyl-2-pyrrolidone
NaCl sodium chloride
$Na_2CO_3$ sodium carbonate
$NaHCO_3$ sodium bicarbonate
NaOH sodium hydroxide
$Na_2SO_4$ sodium sulfate
$NH_4Cl$ ammonium chloride
$NH_4OAc$ ammonium acetate
$Pd(OAc)_2$ palladium(II) acetate
$Pd(PPh_3)_4$ tetrakis(triphenylphosphine)palladium(0)

Rt retention time
$SiO_2$ silica oxide
$SOCl_2$ thionyl chloride
TEA triethylamine
TFA trifluoroacetic acid
THF tetrahydrofuran
T3P® 1-propanephosphonic acid cyclic anhydride Normal phase chromatography was carried out using prepacked $SiO_2$ cartridges. Reverse phase preparative HPLC of Examples was carried out using Waters XBridge C18 column (19×200 mm, 5-μm particles) with UV and LCMS detection using variable gradients of mobile phase A (95% water, 5% ACN) and mobile phase B (5% water, 95% ACN) containing 0.1% TFA or 10 mM $NH_4OAc$. Reverse phase analytical HPLC/MS of Examples was performed on a Waters Acquity system coupled with a Waters MICROMASS® ZQ Mass Spectrometer.

Method A: Linear gradient of 0 to 100% B over 3 min, with 0.75 min hold time at 100% B;
UV visualization at 220 nm
Column: Waters BEH C18 2.1×50 mm
Flow rate: 1.0 mL/min
Solvent A: 10 mM $NH_4OAc$, 95% water, 5% ACN
Solvent B: 10 mM $NH_4OAc$, 5% water, 95% ACN
Method B: Linear gradient of 0 to 100% B over 3 min, with 0.75 min hold time at 100% B;
UV visualization at 220 nm
Column: Waters BEH C18 2.1×50 mm
Flow rate: 1.0 mL/min
Solvent A: 0.1% TFA, 95% water, 5% ACN
Solvent B: 0.1% TFA, 5% water, 95% ACN Synthetic Method 1 ((3S,4R)-3-[(6-chloro-1,3-benzoxazol-2-yl)amino]-4-(2,6-difluoro-4-methoxyphenyl)pyrrolidin-2-one, Example 1)

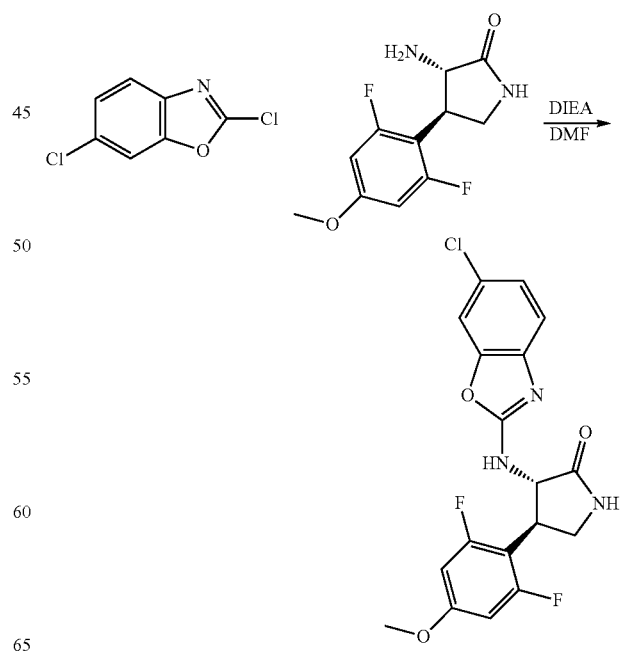

To a solution of (3S,4R)-3-amino-4-(2,6-difluoro-4-methoxyphenyl)pyrrolidin-2-one (13 mg, 0.054 mmol) in ACN (0.5 mL) was added DIEA (0.014 mL, 0.081 mmol) followed by 2,6-dichlorobenzo[d]oxazole (11 mg, 0.059 mmol) and the mixture was heated at 80° C. for 5 h. The mixture was allowed to cool to room temperature, filtered and purified by prep HPLC to Example 1 (12 mg, 55% yield). LCMS (Method 1) Rt=1.62 min, m/z=394.1 (M+H). $^1$H NMR (500 MHz, DMSO-d6) δ 8.51 (d, J=8.9 Hz, 1H), 8.20 (s, 1H), 7.49 (s, 1H), 7.25-7.18 (m, 1H), 7.18-7.10 (m, 1H), 6.74 (d, J=10.7 Hz, 2H), 4.60 (t, J=9.9 Hz, 1H), 4.05 (q, J=9.6 Hz, 1H), 3.73 (s, 3H), 3.57-3.49 (m, 1H), 3.39 (t, J=9.6 Hz, 1H).

Example 2 (Table 1) was prepared by as described for Example 1.

Synthetic Method 2 ((3S,4R)-3-{[5-(4-chlorophenyl)-1,3,4-oxadiazol-2-yl]amino}-4-(2,6-difluoro-4-methoxyphenyl)pyrrolidin-2-one, Example 3)

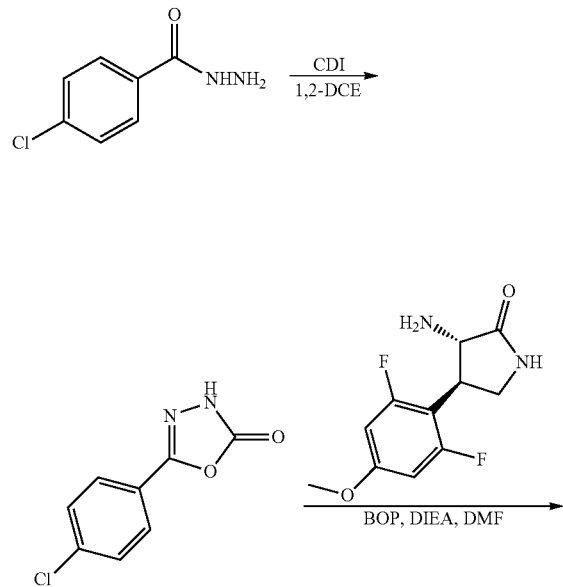

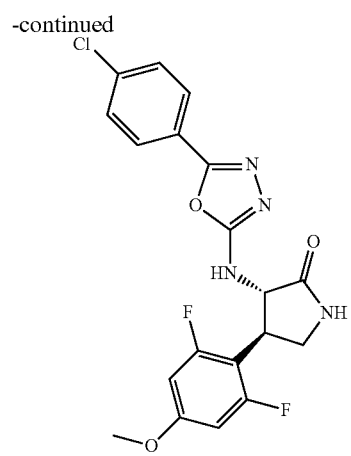

To a suspension of 4-chlorobenzohydrazide (500 mg, 2.9 mmol) in 1,2-dichloroethane (25 mL) in an ice bath was added CDI (570 mg, 3.5 mmol) and the reaction was allowed to warm to room temperature and stirred for 2 h. The mixture was purified on silica gel eluting with 0 to 50% EtOAc/DCM to give 5-(4-chlorophenyl)-1,3,4-oxadiazol-2(3H)-one (430 mg, 2.2 mmol, 75% yield) as a white solid. $^1$H NMR (500 MHz, DMSO-d$_6$) δ 12.65 (s, 1H), 7.90-7.74 (m, 2H), 7.72-7.45 (m, 2H)

To a solution of (3S,4R)-3-amino-4-(2,6-difluoro-4-methoxyphenyl)pyrrolidin-2-one (15 mg, 0.062 mmol) and 5-(4-chlorophenyl)-1,3,4-oxadiazol-2(3H)-one (16 mg, 0.081 mmol) in DMF (0.6 mL) was added DIEA (0.022 mL, 0.12 mmol) followed by BOP (38 mg, 0.087 mmol) and the mixture was stirred for 16 h. The mixture was diluted with water and extracted with EtOAc (3×). The extracts were washed with brine, dried (Na$_2$SO$_4$), filtered and concentrated. The crude product was purified by prep HPLC to give Example 3 (11 mg, 43% yield). LCMS (Method 1) Rt=1.58 min, m/z=421.0 (M+H). $^1$H NMR (500 MHz, DMSO-d$_6$) δ 8.35 (d, J=8.5 Hz, 1H), 8.22 (s, 1H), 7.76 (d, J=8.5 Hz, 2H), 7.58 (d, J=8.5 Hz, 2H), 6.74 (d, J=11.0 Hz, 2H), 4.59-4.44 (m, 1H), 3.98 (q, J=9.8 Hz, 1H), 3.72 (s, 3H), 3.53 (t, J=9.2 Hz, 1H), 3.38 (t, J=9.6 Hz, 1H)

Examples 4-20 (Table 1) were prepared as described for Example 3.

Synthetic Method 3 ((3S,4R)-3-{[5-(4-chlorophenyl)-1,2-oxazol-3-yl]amino}-4-(2,6-difluoro-4-methoxyphenyl)pyrrolidin-2-one, Example 21)

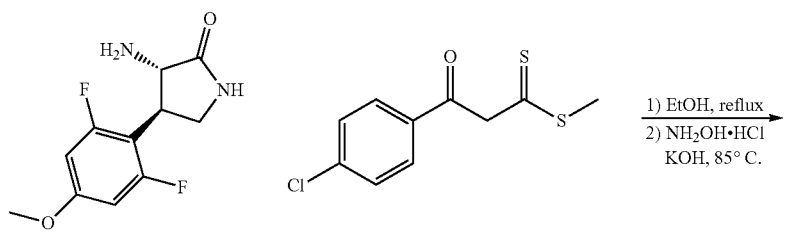

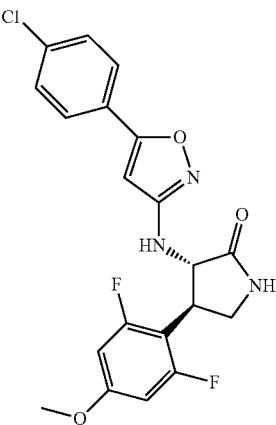

A mixture of (3S,4R)-3-amino-4-(2,6-difluoro-4-methoxyphenyl)pyrrolidin-2-one (30 mg, 0.12 mmol) and methyl 3-(4-chlorophenyl)-3-oxopropanedithioate (30 mg, 0.12 mmol) was refluxed in EtOH (0.6 mL) for 16 h. A solution of hydroxylamine hydrochloride (29 mg, 0.50 mmol) and KOH (35 mg, 0.50 mmol) in water (0.25 mL) was added and the mixture was heated at 85° C. for 16 h. The mixture was diluted with DMF, filtered and purified by prep HPLC to give Example 21 (13 mg, 26% yield). LCMS (Method 1) Rt=1.79 min, m/z=420.4 (M+H). $^1$H NMR (500 MHz, DMSO-d6) δ 8.09 (br s, 1H), 7.80-7.68 (m, 2H), 7.59-7.49 (m, J=8.5 Hz, 2H), 6.78-6.70 (m, 3H), 6.40 (s, 1H), 4.44-4.29 (m, 1H), 3.97 (q, J=9.6 Hz, 1H), 3.74 (s, 3H), 3.57-3.43 (m, 1H), 3.33 (t, J=9.7 Hz, 1H).

Examples 22 and 23 (Table 1) were prepared as described for Example 21.

Synthetic Method 4 ((3S,4R)-3-{[5-(4-chlorophenyl)-1,3-oxazol-2-yl]amino}-4-(2,6-difluoro-4-methoxyphenyl)pyrrolidin-2-one, Example 24)

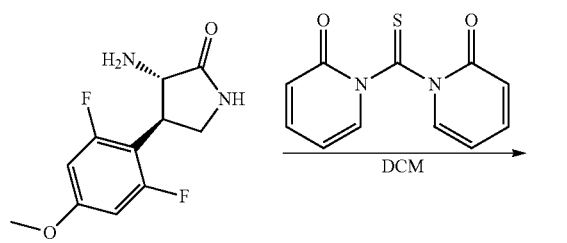

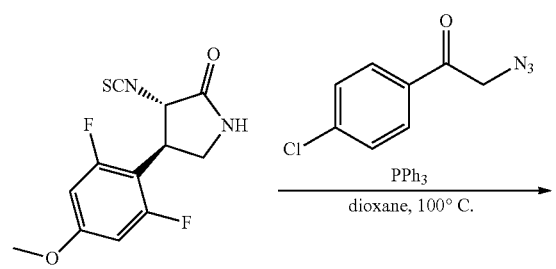

-continued

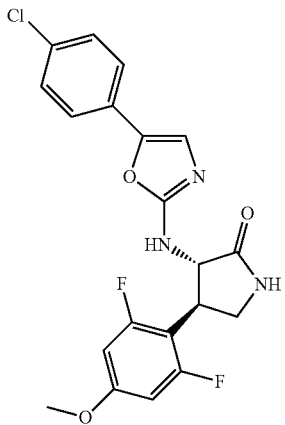

To a solution of (3S,4R)-3-amino-4-(2,6-difluoro-4-methoxyphenyl)pyrrolidin-2-one (100 mg, 0.41 mmol) in DCM (2 mL) was added 1,1'-thiocarbonylbis(pyridin-2(1H)-one) (140 mg, 0.62 mmol). The mixture was stirred for 5 min, loaded onto silica gel and eluted with 5 to 10% EtOAc/DCM to give Example 24 (76 mg, 0.27 mmol, 65% yield) as a white solid. $^1$H NMR (500 MHz, CDCl$_3$) δ 6.83 (s, 1H), 6.54 (d, J=10.5 Hz, 2H), 4.84 (d, J=10.7 Hz, 1H), 4.00 (q, J=9.6 Hz, 1H), 3.83 (s, 3H), 3.67-3.56 (m, 2H)

To a solution of (3S,4R)-4-(2,6-difluoro-4-methoxyphenyl)-3-isothiocyanatopyrrolidin-2-one (15 mg, 0.053 mmol) and 2-azido-1-(4-chlorophenyl)ethanone (12 mg, 0.063 mmol) in dioxane (0.4 mL) was added triphenylphosphine (17 mg, 0.063 mmol) and the mixture was heated at 100° C. for 15 min. The mixture was evaporated and purified by prep HPLC to give Example 24 (13 mg, 57% yield). LCMS (Method 1) Rt=1.70 min, m/z=420.2 (M+H). $^1$H NMR (500 MHz, DMSO-d6) δ 8.15 (s, 1H), 7.91 (d, J=8.9 Hz, 1H), 7.42 (m, 4H), 7.22 (m, 1H), 6.74 (d, J=10.7 Hz, 2H), 4.52 (t, J=9.9 Hz, 1H), 3.97 (q, J=9.5 Hz, 1H), 3.73 (s, 3H), 3.50 (d, J=8.2 Hz, 1H), 3.36 (t, J=9.6 Hz, 1H).

Synthetic Method 5 ((3S,4R)-4-(2,6-difluoro-4-methoxyphenyl)-3-{[5-(4,4-difluorocyclohexyl)-1,3,4-oxadiazol-2-yl]amino}pyrrolidin-2-one, Example 25)

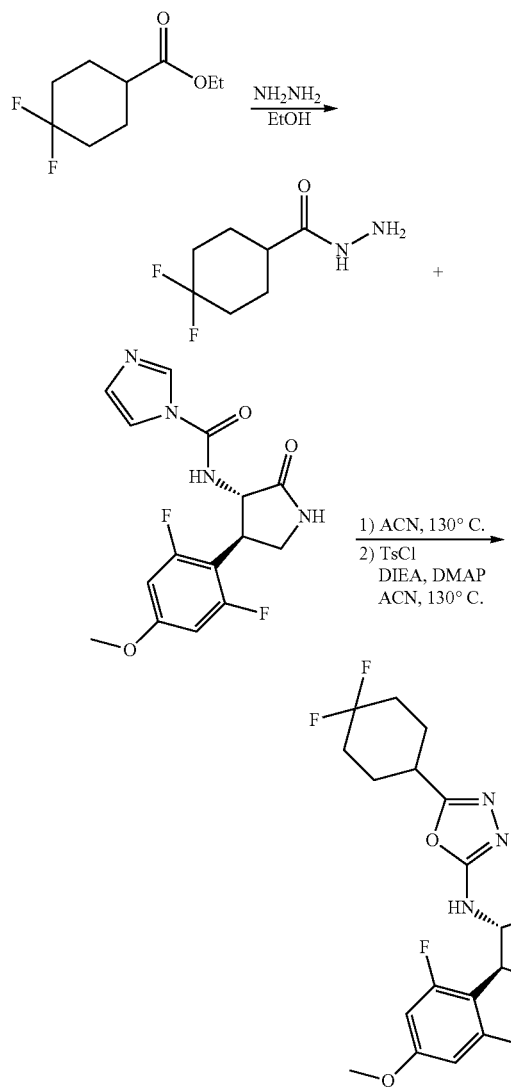

microwave irradiation. The mixture was filtered and purified by prep HPLC to give Example 25 (5.4 mg, 9% yield). LCMS (Method 1) Rt=1.38 min, m/z=429.1 (M+H). $^1$H NMR (500 MHz, DMSO-$d_6$) δ 8.18 (s, 1H), 7.93 (d, J=9.2 Hz, 1H), 6.76 (d, J=10.7 Hz, 2H), 4.45-4.37 (m, 1H), 3.99-3.86 (m, 2H), 3.76 (s, 3H), 3.17 (d, J=5.2 Hz, 1H), 2.95 (t, J=10.5 Hz, 1H), 2.12-1.82 (m, 6H), 1.74-1.56 (m, 2H)

Examples 26 to 28 (Table 1) were prepared as described for Example 25.

Synthetic Method 6 ((3S,4R)-4-(2,6-difluoro-4-methoxyphenyl)-3-[(5-{4-[(trifluoromethyl)sulfanyl]phenyl}-1,3,4-thiadiazol-2-yl)amino]pyrrolidin-2-one, Example 29

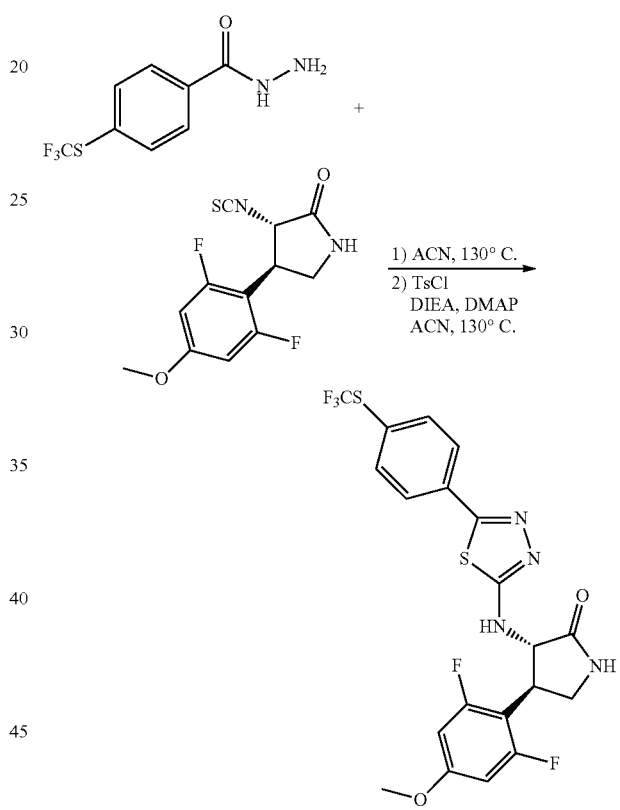

To a solution of ethyl 4,4-difluorocyclohexanecarboxylate (450 mg, 2.3 mmol) in ethanol (3 mL) was added hydrazine (0.37 mL, 12 mmol) and the reaction mixture was stirred at room temperature for 16 h and then concentrated to give 4,4-difluorocyclohexane-1-carbohydrazide (410 mg, 97% yield) as a white solid. $^1$H NMR (500 MHz, CD$_3$OD) δ 2.34-2.24 (m, 1H), 2.18-2.06 (m, 2H), 1.92-1.73 (m, 6H)

To a mixture of 4,4-difluorocyclohexanecarbohydrazide (79 mg, 0.45 mmol) and N-((3S,4R)-4-(2,6-difluoro-4-methoxyphenyl)-2-oxopyrrolidin-3-yl)-1H-imidazole-1-carboxamide (50 mg, 0.15 mmol) in ACN (1 mL) was added DIEA (0.052 mL, 0.30 mmol) and the mixture was heated at 110° C. for 45 min using microwave irradiation. The mixture was allowed to cool to room temperature and then p-toluenesulfonyl chloride (56 mg, 0.29 mmol) was added followed by DIEA (0.051 mL, 0.29 mmol) and DMAP (18 mg, 0.15 mmol). The mixture was heated at 130° C. for 1 h using To a solution of 4-((trifluoromethyl)thio)benzohydrazide (46 mg, 0.19 mmol, prepared as described in Example 25) and (3S,4R)-4-(2,6-difluoro-4-methoxyphenyl)-3-isothiocyanatopyrrolidin-2-one (50 mg, 0.18 mmol, prepared as described in Example 24) in THF (2 mL) was added DIEA (0.15 mL, 0.88 mmol) and the mixture stirred for 3 h. A portion of this material containing N-((3S,4R)-4-(2,6-difluoro-4-methoxyphenyl)-2-oxopyrrolidin-3-yl)-2-(4-((trifluoromethyl)thio)benzoyl)hydrazine-1-carbothioamide (0.096 mmol) was evaporated and dissolved in ACN (1 mL). p-Toluenesulfonyl chloride (55 mg, 0.29 mmol) was added followed by DIEA (0.034 mL, 0.19 mmol) and DMAP (12 mg, 0.096 mmol) and the reaction mixture was heated at 100° C. for 45 min using microwave irradiation. The mixture was filtered and purified by prep HPLC to give Example 29 (40 mg, 83% yield). LCMS (Method 1) Rt=2.00 min, m/z=503.2 (M+H). $^1$H NMR (500 MHz, DMSO-$d_6$) δ 8.52 (d, J=8.4 Hz, 1H), 8.26 (s, 1H), 7.95-7.74 (m, 4H), 6.77 (d, J=10.8 Hz, 2H), 4.74 (dd, J=10.6, 8.7 Hz, 1H), 4.03 (d, J=9.9 Hz, 1H), 3.76 (s, 3H), 3.56 (m, 2H)

Synthetic Method 7 ((3S,4R)-4-(2,6-difluoro-4-methoxyphenyl)-3-({5-[4-(trifluoromethoxy)phenyl]-1,3,4-thiadiazol-2-yl}amino)pyrrolidin-2-one, Example 30)

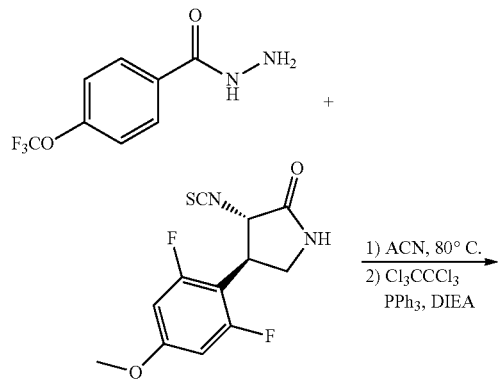

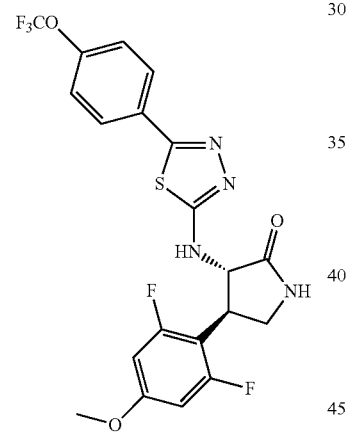

A mixture of 4-(trifluoromethoxy)benzohydrazide (15 mg, 0.067 mmol, prepared as described in Example 25) and (3S,4R)-4-(2,6-difluoro-4-methoxyphenyl)-3-isothiocyanatopyrrolidin-2-one (19 mg, 0.067 mmol, prepared as described in Example 24) in ACN (0.7 mL) was heated at 80° C. for 1 h and allowed to cool to room temperature. To this mixture was added a solution of triphenylphosphine (35 mg, 0.13 mmol), hexachloroethane (32 mg, 0.13 mmol) and DIEA (0.047 mL, 0.27 mmol) in ACN (0.7 mL) and the resulting mixture was stirred for 1 h. The mixture was filtered and purified by prep HPLC to give Example 30 (15 mg, 46% yield). LCMS (Method 1) Rt=1.84 min, m/z=487.2 (M+H). $^1$H NMR (500 MHz, DMSO-d6) δ 8.18 (s, 1H), 7.84 (br d, J=8.5 Hz, 2H), 7.45 (br d, J=8.2 Hz, 2H), 6.73 (br d, J=11.0 Hz, 2H), 4.70 (br t, J=9.6 Hz, 1H), 4.10-3.95 (m, 1H), 3.74 (s, 3H), 3.54 (br t, J=8.7 Hz, 1H), 3.38 (br t, J=9.5 Hz, 1H)

Examples 31 to 33 (Table 1) were prepared as described for Example 30.

Synthetic Method 8 ((3S,4R)-3-{[5-(4-butoxyphenyl)-1,3,4-oxadiazol-2-yl]amino}-4-(2,6-difluoro-4-methoxyphenyl)pyrrolidin-2-one, Example 34)

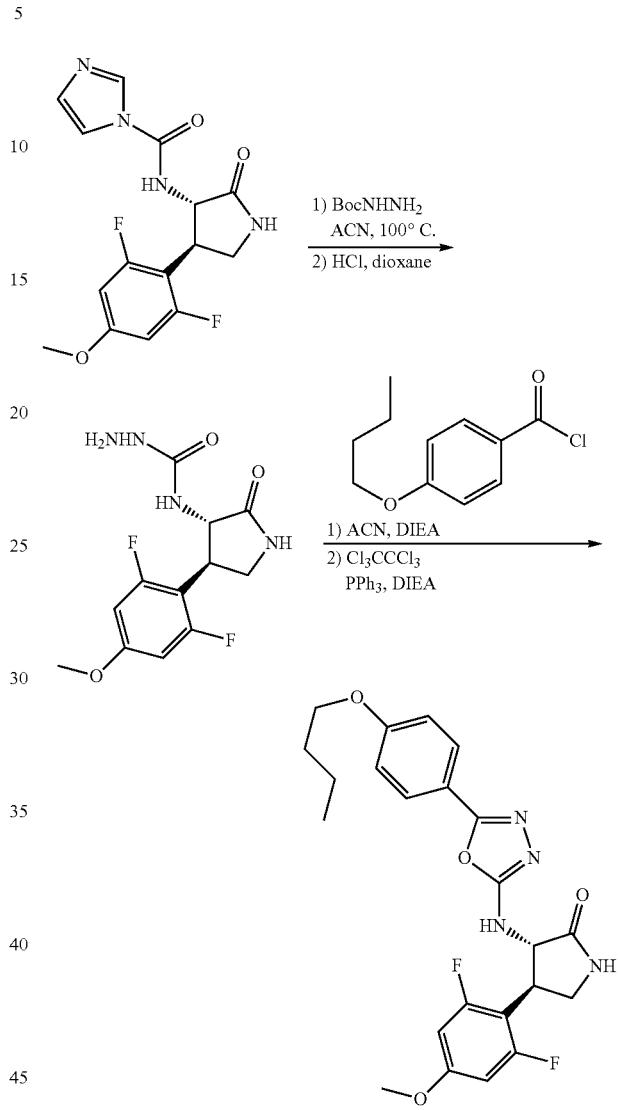

A mixture of N-((3S,4R)-4-(2,6-difluoro-4-methoxyphenyl)-2-oxopyrrolidin-3-yl)-1H-imidazole-1-carboxamide (720 mg, 2.1 mmol) and tert-butyl hydrazinecarboxylate (290 mg, 2.2 mmol) in ACN (11 mL) was heated at 100° C. for 1 h. The mixture was allowed to cool to room temperature and the solvent was removed under reduced pressure. The residue was treated with 4M HCl in dioxane (2 mL, 8.0 mmol) and stirred for 1 h. The mixture was concentrated under reduced pressure, diluted with 1.5 M K$_2$HSO$_4$ (aq) and extracted with DCM. The combined organic fractions were concentrated under reduced pressure, diluted with water and the solid collected by filtration. The solid was washed with water and dried under vacuum to give N-((3S,4R)-4-(2,6-difluoro-4-methoxyphenyl)-2-oxopyrrolidin-3-yl)hydrazinecarboxamide (360 mg, 1.2 mmol, 57% yield) as a white solid. LCMS (Method 1) Rt=0.47 min, m/z=301.1 (M+H).

To a solution of N-((3S,4R)-4-(2,6-difluoro-4-methoxyphenyl)-2-oxopyrrolidin-3-yl)hydrazinecarboxamide (12 mg, 0.040 mmol) in ACN (1.0 mL) was added DIEA (0.013 mL, 0.077 mmol) and 4-butoxybenzoyl chloride (9.0 mg, 0.042 mmol) and the mixture was stirred at room temperature for 1 h. To this mixture was added a solution of triphenylphosphine (30 mg, 0.12 mmol), hexachloroethane (27 mg, 0.12 mmol) and DIEA (0.040 mL, 0.23 mmol) in ACN (0.5 mL) and the resulting mixture was stirred for 1 h. The mixture was filtered and purified by prep HPLC to give Example 34 (2.4 mg, 13% yield). LCMS (Method 1) Rt=1.85 min, m/z=459.5 (M+H). $^1$H NMR (500 MHz, DMSO-$d_6$) δ 8.21 (s, 1H), 8.17 (br d, J=8.9 Hz, 1H), 7.67 (d, J=8.5 Hz, 2H), 7.05 (br d, J=8.9 Hz, 2H), 6.75 (br d, J=10.7 Hz, 2H), 4.56-4.43 (m, 1H), 4.02 (t, J=6.4 Hz, 2H), 4.01-3.93 (m, 1H), 3.61-3.47 (m, 1H), 3.44-3.30 (m, 4H), 1.75-1.64 (m, 2H), 1.43 (sxt, J=7.4 Hz, 2H), 0.93 (t, J=7.3 Hz, 3H)

Synthetic Method 9 ((3S,4R)-4-(2,6-difluoro-4-methoxyphenyl)-3-{[5-(4-phenoxyphenyl)-1,3,4-oxadiazol-2-yl]amino}pyrrolidin-2-one, Example 35)

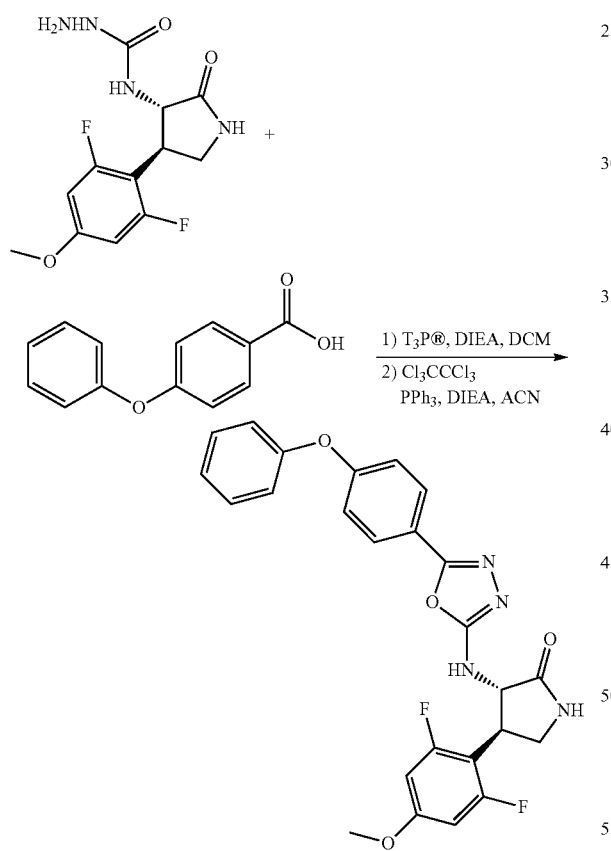

In a pressure resistant vial, a suspension of N-((3S,4R)-4-(2,6-difluoro-4-methoxyphenyl)-2-oxopyrrolidin-3-yl)hydrazinecarboxamide (20 mg, 0.067 mmol, prepared as described in Example 34) in DCM (1.0 mL) was prepared. DIEA (0.014 mL, 0.080 mmol) was added followed by 4-phenoxybenzoic acid (17.12 mg, 0.080 mmol) and 50% T3P® in EtOAc (0.048 mL, 0.080 mmol). The mixture was stirred at 60° C. for 16 h and then allowed to cool to room temperature. To this mixture was added a solution of triphenylphosphine (70 mg, 0.26 mmol), hexachloroethane (64 mg, 0.26 mmol) and DIEA (0.094 mL, 0.53 mmol) in ACN (1 mL) and the mixture was stirred for 3 h. The mixture was filtered and purified by prep HPLC to give Example 35 (5.3 mg, 17% yield). LCMS (Method 1) Rt=1.77 min, m/z=479.2 (M+H). $^1$H NMR (500 MHz, DMSO-$d_6$) δ 8.29 (d, J=8.8 Hz, 1H), 8.27-8.16 (m, 1H), 7.75 (d, J=8.8 Hz, 2H), 7.44 (t, J=7.9 Hz, 2H), 7.22 (t, J=7.4 Hz, 1H), 7.12-7.04 (m, 4H), 6.72 (br d, J=10.8 Hz, 2H), 4.58-4.45 (m, 1H), 4.08-3.99 (m, 1H), 3.71 (s, 3H), 3.53 (br t, J=9.0 Hz, 1H), 3.44-3.32 (m, 1H)

Examples 36 and 37 (Table 1) were prepared as described for Example 35.

Synthetic Method 10 ((3S,4R)-3-{[5-(4-cyclopropylphenyl)-1,3,4-oxadiazol-2-yl]amino}-4-(2,6-difluoro-4-methoxyphenyl)pyrrolidin-2-one, Example 38)

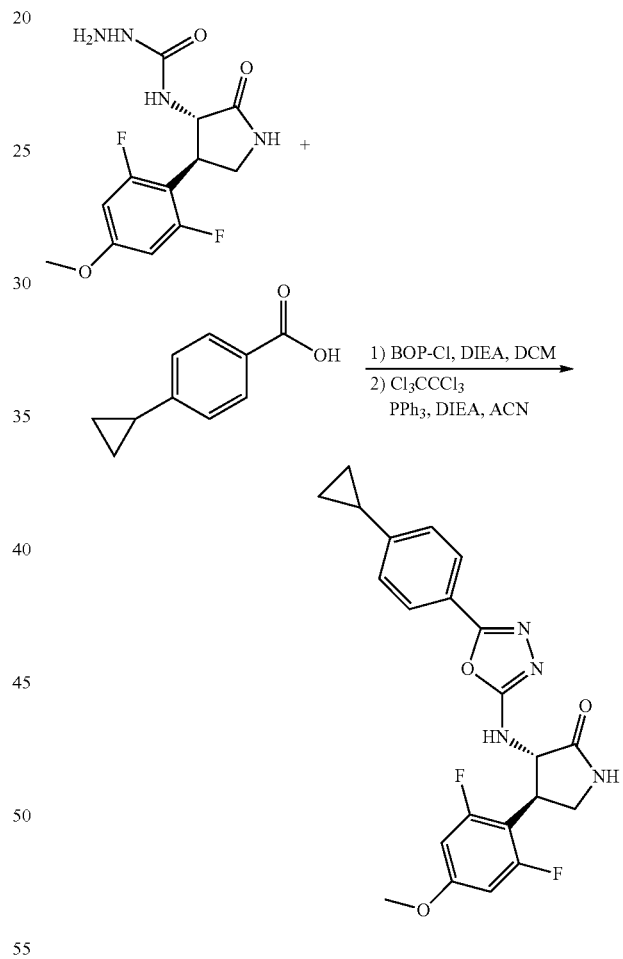

To a solution of N-((3S,4R)-4-(2,6-difluoro-4-methoxyphenyl)-2-oxopyrrolidin-3-yl)hydrazinecarboxamide (23 mg, 0.077 mmol), 4-cyclopropylbenzoic acid (14 mg, 0.084 mmol) and DIEA (0.016 mL, 0.092 mmol) in ACN (1.0 mL) was added BOP-Cl (23 mg, 0.092 mmol) and the mixture was stirred 1 h. A solution of triphenylphosphine (80 mg, 0.30 mmol) and hexachloroethane (72 mg, 0.30 mmol) in ACN (1.6 mL) was added and the mixture was stirred for 2 h. The mixture was filtered and purified by prep HPLC to give Example 38 mg, 52% yield). LCMS (Method 1) Rt=1.60 min, m/z=427.0 (M+H). $^1$H NMR (500 MHz, DMSO-$d_6$) δ 8.29-8.18 (m, 2H), 7.69-7.56 (m, 2H), 7.21 (br d, J=8.2 Hz, 2H), 6.76 (br d, J=10.7 Hz, 2H), 4.51 (dd, J=10.8, 9.3 Hz, 1H), 4.03-3.94 (m, 1H), 3.74 (s, 3H), 3.53-3.43 (m, 1H), 3.37 (br d, J=8.9 Hz, 1H), 2.04-1.93 (m, 1H), 1.09-0.94 (m, 2H), 0.74 (dd, J=4.6, 1.5 Hz, 2H)

Examples 39 to 46 (Table 1) were prepared as described for Example 38.

Synthetic Method 11 ((3S,4R)-4-(2,6-difluoro-4-methoxyphenyl)-3-({5-[4-(4,4,4-trifluorobutoxy)phenyl]-1,3,4-oxadiazol-2-yl}amino)pyrrolidin-2-one, Example 47)

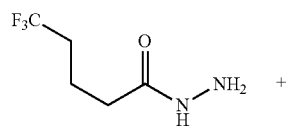

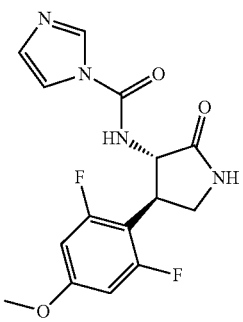

A mixture of N-((3S,4R)-4-(2,6-difluoro-4-methoxyphenyl)-2-oxopyrrolidin-3-yl)-1H-imidazole-1-carboxamide (50 mg, 0.15 mmol) and 4-(4,4,4-trifluorobutoxy)benzohydrazide (39 mg, 0.15 mmol, prepared as described in Example 5) in ACN (14 mL) was heated at 80° C. for 3 h and allowed to cool to room temperature. A solution of triphenylphosphine (160 mg, 0.60 mmol), hexachloroethane (140 mg, 0.60 mmol) and DIEA (0.21 mL, 1.2 mmol) in ACN (2 mL) was added and the mixture was stirred for 1 h. The mixture was concentrated under reduced pressure, dissolved in DMF, filtered and purified by prep HPLC to give Example 47 (52 mg, 68% yield). LCMS (Method 2) Rt=1.76 min, m/z=513.0 (M+H). $^1$H NMR (500 MHz, DMSO-$d_6$) δ 8.10 (s, 1H), 8.04 (br d, J=8.8 Hz, 1H), 7.69 (d, J=8.8 Hz, 2H), 7.09 (d, J=8.8 Hz, 2H), 6.74 (br d, J=10.7 Hz, 2H), 4.56-4.47 (m, 1H), 4.13 (t, J=6.2 Hz, 2H), 4.01 (q, J=9.6 Hz, 1H), 3.76 (s, 3H), 3.54 (br t, J=9.2 Hz, 1H), 3.39 (br t, J=9.4 Hz, 1H), 2.48-2.37 (m, 2H), 2.03-1.92 (m, 2H)

Synthetic Method 12 ((3S,4R)-3-[(6-chloro-1,2-benzoxazol-3-yl)amino]-4-(2,6-difluoro-4-methoxyphenyl)pyrrolidin-2-one, Example 50)

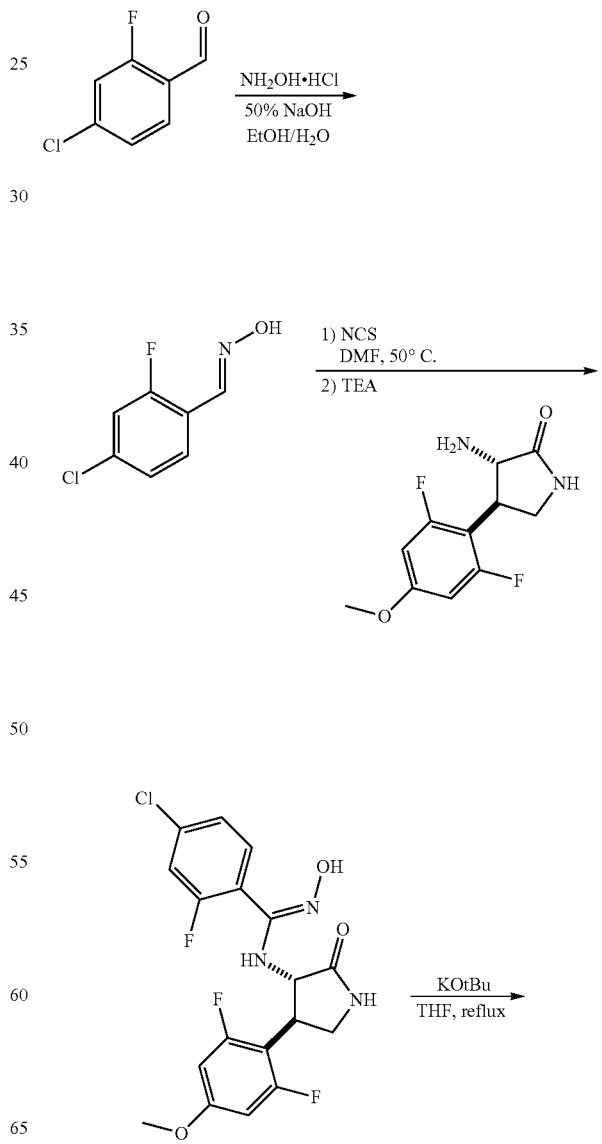

-continued

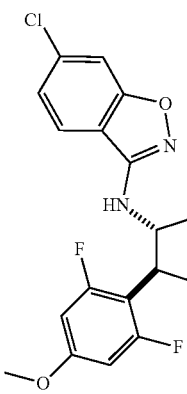

To a mixture of 4-chloro-2-fluorobenzaldehyde (1.0 g, 6.3 mmol) in ethanol (20 mL) and water (40 mL) was added hydroxylamine hydrochloride (0.48 g, 6.4 mmol) followed by 50% (w/w) NaOH in water (1.3 mL) and the mixture was stirred for 1 h. The solution was neutralized with conc HCl then extracted with DCM (3×). The extracts were washed with brine, dried ($Na_2SO_4$), filtered and concentrated under reduced pressure to give 4-chloro-2-fluorobenzaldehyde oxime (1.0 g, 5.8 mmol, 92% yield) as a white solid. $^1$H NMR (500 MHz, CDCl$_3$) δ 8.34 (s, 1H), 7.78-7.69 (m, 2H), 7.19 (d, J=8.8 Hz, 1H), 7.17 (d, J=9.1 Hz, 1H) To a solution of 4-chloro-2-fluorobenzaldehyde oxime (25 mg, 0.14 mmol) in DMF (1.5 mL) was added NCS (19 mg, 0.14 mmol) and the mixture heated at 50° C. for 0.5 h. The mixture was allowed to cool to room temperature. (3S,4R)-3-amino-4-(2,6-difluoro-4-methoxyphenyl)pyrrolidin-2-one (35 mg, 0.14 mmol) was added followed by DIEA (0.030 mL, 0.17 mmol) and the mixture was stirred for 0.5 h. The mixture was diluted with water and extracted with 50% EtOAc/hexanes (3×). The extracts were dried ($Na_2SO_4$), filtered and concentrated under reduced pressure. The residue was purified on silica gel, eluting with 0.2 to 12% MeOH/DCM to give 4-chloro-N-((3S,4R)-4-(2,6-difluoro-4-methoxyphenyl)-2-oxopyrrolidin-3-yl)-2-fluoro-N'-hydroxybenzimidamide (31 mg, 0.071 mmol, 49% yield) as a white solid. $^1$H NMR (500 MHz, CDCl$_3$ containing CD$_3$OD) δ 7.06-6.92 (m, 3H), 6.38 (br d, J=10.7 Hz, 2H), 4.22 (d, J=10.7 Hz, 1H), 3.82 (s, 3H), 3.73 (q, J=9.9 Hz, 1H), 3.48-3.40 (m, 1H), 3.38-3.31 (m, 1H)

To a solution of 4-chloro-N-((3S,4R)-4-(2,6-difluoro-4-methoxyphenyl)-2-oxopyrrolidin-3-yl)-2-fluoro-N'-hydroxybenzimidamide (30 mg, 0.073 mmol) in THF (1 mL) was added potassium tert-butoxide (9.0 mg, 0.080 mmol) and the mixture was heated at reflux for 1 h. The mixture was allowed to cool to room temperature and evaporated under reduced vacuum. The residue was diluted with satd NH$_4$Cl and extracted with DCM (3×). The extracts were dried (Na$_2$SO$_4$), filtered and concentrated under reduced pressure. The crude producte was purified by prep HPLC to give Example 50 (19 mg, 67% yield). LCMS (Method 1) Rt=1.67 min, m/z=394.0 (M+H). $^1$H NMR (500 MHz, DMSO-d$_6$) δ 8.16 (s, 1H), 7.78 (d, J=8.5 Hz, 1H), 7.64 (s, 1H), 7.61-7.47 (m, 1H), 7.32 (br d, J=8.5 Hz, 1H), 6.72 (br d, J=11.0 Hz, 2H), 4.58-4.48 (m, 1H), 4.13 (q, J=9.7 Hz, 1H), 3.67-3.60 (m, 1H), 3.38 (br t, J=9.6 Hz, 1H), 2.55 (s, 3H)

Example 51 (Table 1) was prepared as described for Example 50.

Synthetic Method 13 (2-[(3S,4R)-3-{[5-(4-chlorophenyl)-1,3,4-oxadiazol-2-yl]amino}-4-(2,6-difluoro-4-methoxyphenyl)-2-oxopyrrolidin-1-yl]acetic acid, Example 52)

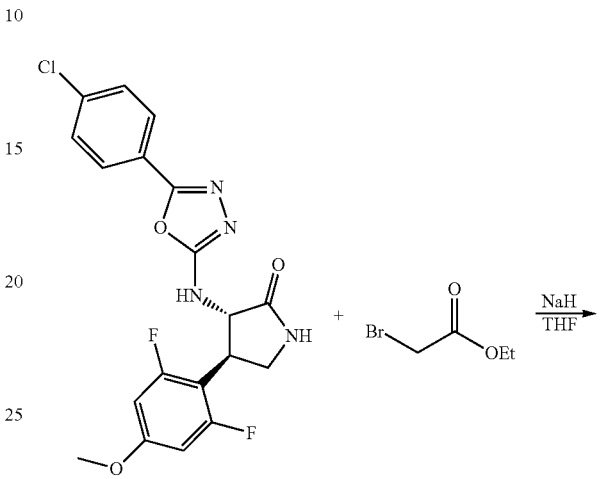

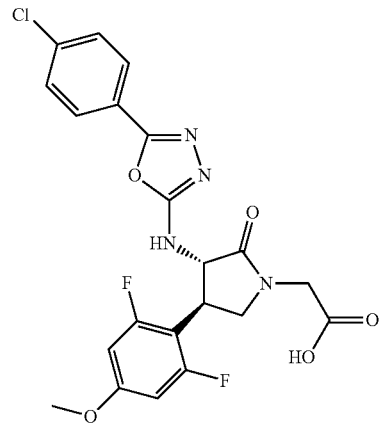

To a solution of (3S,4R)-3-((5-(4-chlorophenyl)-1,3,4-oxadiazol-2-yl)amino)-4-(2,6-difluoro-4-methoxyphenyl)pyrrolidin-2-one (7.0 mg, 0.017 mmol) and ethyl 2-bromoacetate (2.8 mg, 0.017 mmol) in THF (0.3 mL) was added a 60% suspension of NaH in mineral oil (1.8 mg, 0.075 mmol) and the mixture was stirred for 16 h. The mixture was quenched with MeOH, concentrated under reduced pressure and purified by prep HPLC to give Example 52. LCMS (Method 2) Rt=1.53 min, m/z=479.0 (M+H). $^1$H NMR (500 MHz, DMSO-d6) δ 7.78 (d, J=8.2 Hz, 2H), 7.59 (d, J=8.5 Hz, 2H), 6.77 (d, J=10.7 Hz, 1H), 4.66 (s, 2H), 4.07-3.80 (m, 3H), 3.75 (s, 3H), 3.69-3.59 (m, 1H), 1.24 (s, 1H), 1.00 (d, J=6.1 Hz, 1H)

Synthetic Method 14 (N-[(4-chlorophenyl)methyl]-5-{[(3S,4R)-4-(2,6-difluoro-4-methoxyphenyl)-2-oxopyrrolidin-3-yl]amino}-1,3,4-oxadiazole-2-carboxamide, Example 53)

Synthetic Method 15 ((3S,4R)-3-[(5-{4-[(5-chloro-pyridin-2-yl)oxy]phenyl}-1,3,4-oxadiazol-2-yl)amino]-4-(2,6-difluoro-4-methoxyphenyl)pyrrolidin-2-one, Example 55)

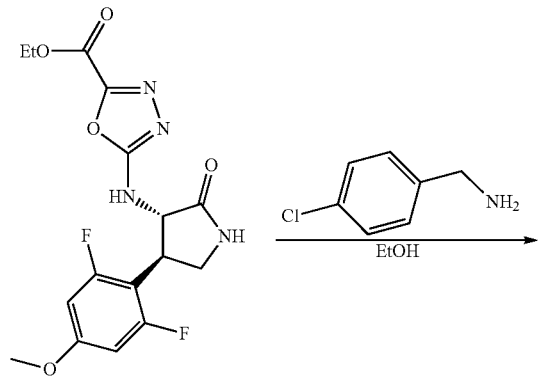

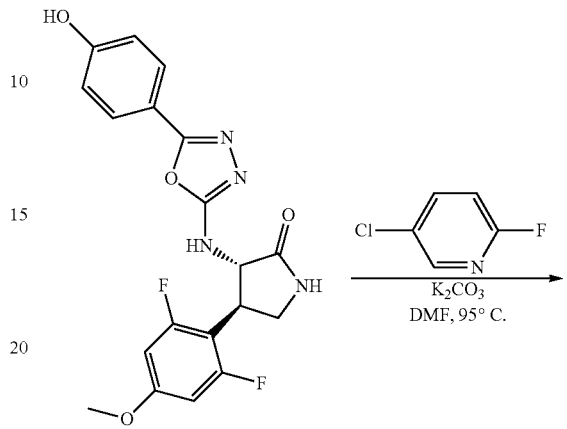

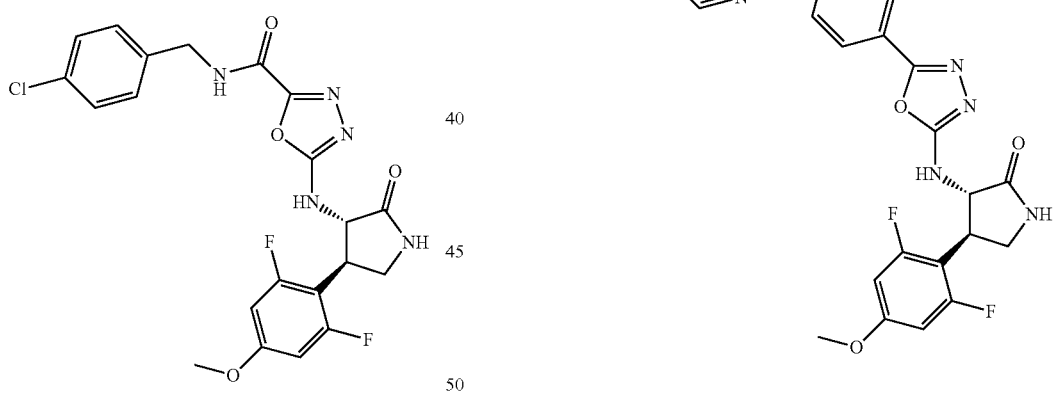

To a solution of ethyl 5-(((3S,4R)-4-(2,6-difluoro-4-methoxyphenyl)-2-oxopyrrolidin-3-yl)amino)-1,3,4-oxadiazole-2-carboxylate (8.5 mg, 0.022 mmol, prepared as described for Example 47) in ethanol (0.2 mL) was added 4-chlorobenzylamine (5.4 µl, 0.044 mmol) and the mixture was heated at 50° C. for 16 h. The mixture was allowed to cool to room temperature, filtered and purified by prep HPLC to give Example 53 (3.5 mg, 32% yield). LCMS (Method 1) Rt=1.61 min, m/z=478.0 (M+H). $^1$H NMR (500 MHz, DMSO-d$_6$) δ 9.30 (t, J=6.1 Hz, 1H), 8.12 (s, 1H), 7.39-7.34 (m, 2H), 7.34-7.29 (m, 2H), 6.73 (d, J=10.7 Hz, 2H), 4.58-4.45 (m, 2H), 4.39 (d, J=6.1 Hz, 4H), 4.02-3.93 (m, 1H), 3.59-3.46 (m, 2H)

Example 54 (Table 1) was prepared as described for Example 53.

To a solution of (3S,4R)-4-(2,6-difluoro-4-methoxyphenyl)-3-((5-(4-hydroxyphenyl)-1,3,4-oxadiazol-2-yl)amino)pyrrolidin-2-one (20 mg, 0.050 mmol, prepared as described for Example 47) in DMF (0.5 mL) was added 5-chloro-2-fluoropyridine (7.9 mg, 0.060 mmol) followed by K$_2$CO$_3$ (10 mg, 0.075 mmol) and the mixture was stirred at 95° C. for 16 h. The mixture was allowed to cool to room temperature, filtered and purified by prep HPLC to give Example 55 (7.3 mg, 29% yield). LCMS (Method 1) Rt=1.74 min, m/z=514.3 (M+H). $^1$H NMR (500 MHz, DMSO-d$_6$) δ 8.28 (d, J=8.9 Hz, 1H), 8.24 (s, 2H), 8.05-7.97 (m, 1H), 7.80 (d, J=8.5 Hz, 2H), 7.29 (d, J=8.5 Hz, 2H), 7.22-7.13 (m, 1H), 6.82-6.71 (m, 1H), 6.77 (d, J=10.7 Hz, 1H), 4.61-4.47 (m, 1H), 3.99 (q, J=9.7 Hz, 1H), 3.75 (s, 3H), 2.56-2.53 (m, 2H)

Examples 48-49 and 56 to 68 (Table 1) were prepared as described for Example 55.

TABLE 1

| Ex. No. | Name | Structure | LC/MS Rt Method M + H |
|---|---|---|---|
| 2 | (3S,4R)-3-{[5-(4-chlorophenyl)-1,3,4-thiadiazol-2-yl]amino}-4-(2,6-difluoro-4-methoxyphenyl)pyrrolidin-2-one | 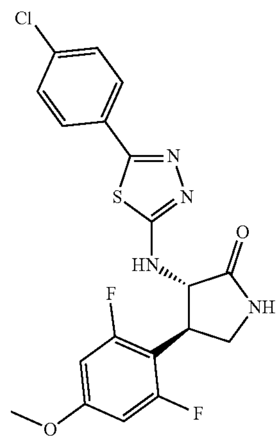 [SMILES: COc1cc(F)c([C@@H]2CNC(=O)[C@H]2Nc2nnc(-c3ccc(Cl)cc3)s2)c(F)c1] | 1.67 min (Method 1) 437.2 |
| 4 | (3S,4R)-4-(2,6-difluoro-4-methoxyphenyl)-3-[(5-phenyl-1,3,4-oxadiazol-2-yl)amino]pyrrolidin-2-one | 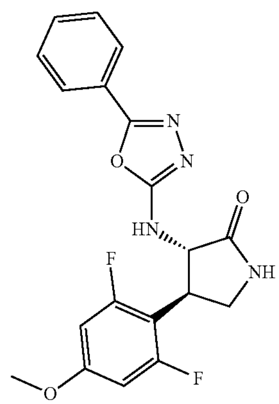 [SMILES: COc1cc(F)c([C@@H]2CNC(=O)[C@H]2Nc2nnc(-c3ccccc3)o2)c(F)c1] | 1.52 min (Method 2) 386.9 |
| 5 | (3S,4R)-4-(2,6-difluoro-4-methoxyphenyl)-3-{[5-(3,4-difluorophenyl)-1,3,4-oxadiazol-2-yl]amino}pyrrolidin-2-one | 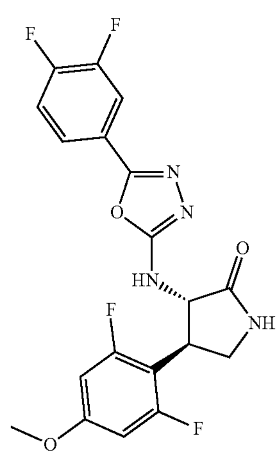 [SMILES: COc1cc(F)c([C@@H]2CNC(=O)[C@H]2Nc2nnc(-c3ccc(F)c(F)c3)o2)c(F)c1] | 1.47 min (Method 2) 423.2 |

TABLE 1-continued

| Ex. No. | Name | Structure | LC/MS Rt Method M + H |
|---|---|---|---|
| 6 | (3S,4R)-4-(2,6-difluoro-4-methoxyphenyl)-3-{[5-(pyridin-3-yl)-1,3,4-oxadiazol-2-yl]amino}pyrrolidin-2-one | 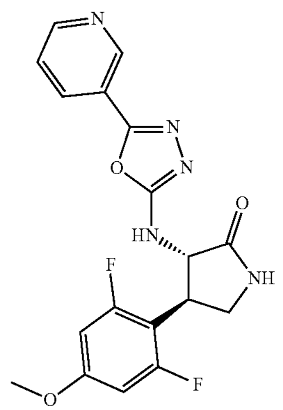 [SMILES: COc1cc(F)c([C@@H]2CNC(=O)[C@H]2Nc2nnc(-c3cccnc3)o2)c(F)c1] | 1.03 min (Method 1) 388.2 |
| 7 | (3S,4R)-4-(2,6-difluoro-4-methoxyphenyl)-3-({5-[4-(trifluoromethoxy)phenyl]-1,3,4-oxadiazol-2-yl}amino)pyrrolidin-2-one | 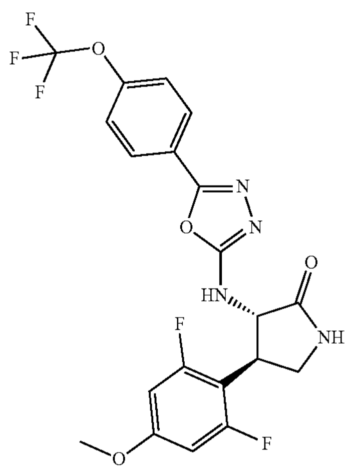 [SMILES: COc1cc(F)c([C@@H]2CNC(=O)[C@H]2Nc2nnc(-c3ccc(OC(F)(F)F)cc3)o2)c(F)c1] | 1.72 min (Method 1) 471.4 |
| 8 | (3S,4R)-4-(2,6-difluoro-4-methoxyphenyl)-3-({5-[4-(trifluoromethyl)phenyl]-1,3,4-oxadiazol-2-yl}amino)pyrrolidin-2-one | 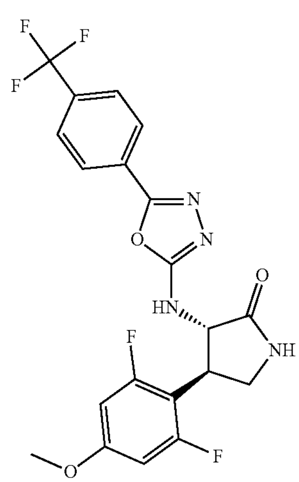 [SMILES: COc1cc(F)c([C@@H]2CNC(=O)[C@H]2Nc2nnc(-c3ccc(C(F)(F)F)cc3)o2)c(F)c1] | 1.64 min (Method 2) 455.2 |

TABLE 1-continued

| Ex. No. | Name | Structure | LC/MS Rt Method M + H |
|---|---|---|---|
| 9 | 4-(5-{[(3S,4R)-4-(2,6-difluoro-4-methoxyphenyl)-2-oxopyrrolidin-3-yl]amino}-1,3,4-oxadiazol-2-yl)benzonitrile | 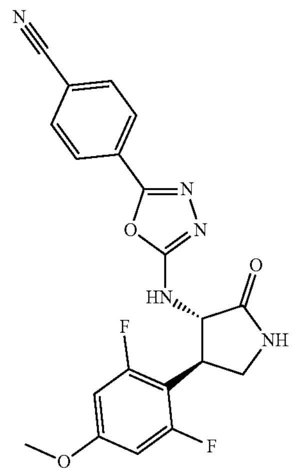 [SMILES: COc1cc(F)c([C@@H]2CNC(=O)[C@H]2Nc2nnc(-c3ccc(C#N)cc3)o2)c(F)c1] | 1.32 min (Method 1) 412.2 |
| 10 | (3S,4R)-4-(2,6-difluoro-4-methoxyphenyl)-3-({5-[6-(trifluoromethyl)pyridin-3-yl]-1,3,4-oxadiazol-2-yl}amino)pyrrolidin-2-one | 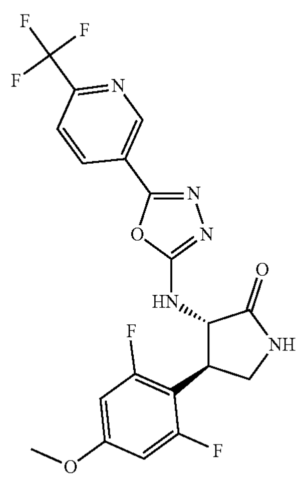 [SMILES: COc1cc(F)c([C@@H]2CNC(=O)[C@H]2Nc2nnc(-c3ccc(C(F)(F)F)nc3)o2)c(F)c1] | 1.47 min (Method 1) 456.2 |
| 11 | (3S,4R)-4-(2,6-difluoro-4-methoxyphenyl)-3-{[5-(4-methylphenyl)-1,3,4-oxadiazol-2-yl]amino}pyrrolidin-2-one | 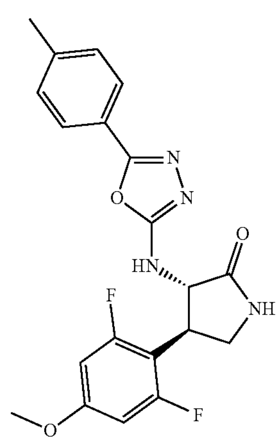 [SMILES: COc1cc(F)c([C@@H]2CNC(=O)[C@H]2Nc2nnc(-c3ccc(C)cc3)o2)c(F)c1] | 1.46 min (Method 2) 401.2 |

TABLE 1-continued

| Ex. No. | Name | Structure | LC/MS Rt Method M + H |
|---|---|---|---|
| 12 | (3S,4R)-4-(2,6-difluoro-4-methoxyphenyl)-3-{[5-(4-fluorophenyl)-1,3,4-oxadiazol-2-yl]amino}pyrrolidin-2-one | 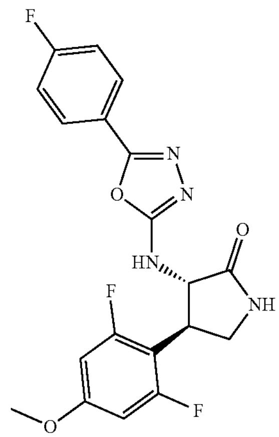 [SMILES: COc1cc(F)c([C@@H]2CNC(=O)[C@H]2Nc2nnc(-c3ccc(F)cc3)o2)c(F)c1] | 1.44 min (Method 1) 404.8 |
| 13 | (3S,4R)-4-(2,6-difluoro-4-methoxyphenyl)-3-({5-[4-(1H-pyrazol-1-yl)phenyl]-1,3,4-oxadiazol-2-yl}amino)pyrrolidin-2-one | 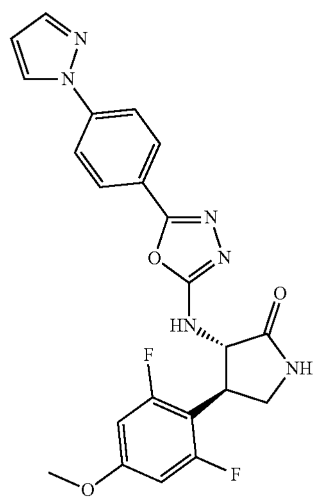 [SMILES: COc1cc(F)c([C@@H]2CNC(=O)[C@H]2Nc2nnc(-c3ccc(-n4cccn4)cc3)o2)c(F)c1] | 1.37 min (Method 1) 453.3 |
| 14 | (3S,4R)-4-(2,6-difluoro-4-methoxyphenyl)-3-({5-[5-(trifluoromethyl)pyridin-2-yl]-1,3,4-oxadiazol-2-yl}amino)pyrrolidin-2-one | 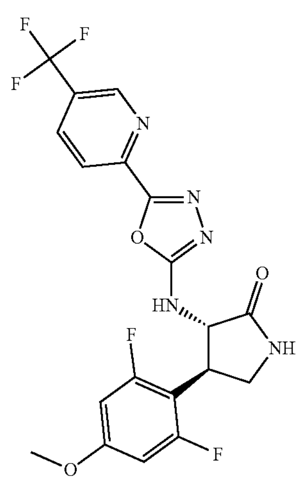 [SMILES: COc1cc(F)c([C@@H]2CNC(=O)[C@H]2Nc2nnc(-c3ccc(C(F)(F)F)cn3)o2)c(F)c1] | 1.43 min (Method 1) 456.3 |

TABLE 1-continued

| Ex. No. | Name | Structure | LC/MS Rt Method M + H |
|---|---|---|---|
| 15 | (3S,4R)-3-{[5-(4-chloro-2-fluorophenyl)-1,3,4-oxadiazol-2-yl]amino}-4-(2,6-difluoro-4-methoxyphenyl)pyrrolidin-2-one | 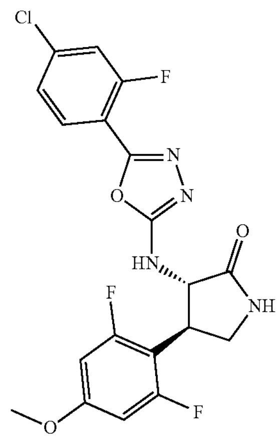 [SMILES: COc1cc(F)c([C@@H]2CNC(=O)[C@H]2Nc2nnc(-c3ccc(Cl)cc3F)o2)c(F)c1] | 1.53 min (Method 1) 439.2 |
| 16 | (3S,4R)-3-{[5-(6-chloropyridin-3-yl)-1,3,4-oxadiazol-2-yl]amino}-4-(2,6-difluoro-4-methoxyphenyl)pyrrolidin-2-one | 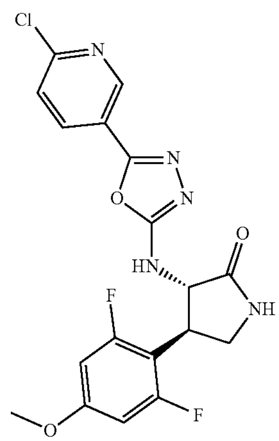 [SMILES: COc1cc(F)c([C@@H]2CNC(=O)[C@H]2Nc2nnc(-c3ccc(Cl)nc3)o2)c(F)c1] | 1.29 min (Method 1) 422.2 |
| 17 | (3S,4R)-4-(2,6-difluoro-4-methoxyphenyl)-3-({5-[4-(difluoromethyl)phenyl]-1,3,4-oxadiazol-2-yl}amino)pyrrolidin-2-one | 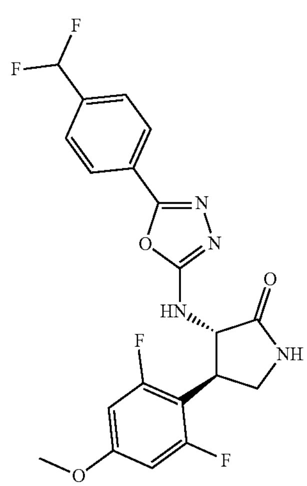 [SMILES: COc1cc(F)c([C@@H]2CNC(=O)[C@H]2Nc2nnc(-c3ccc(C(F)F)cc3)o2)c(F)c1] | 1.46 min (Method 2) 437.3 |

TABLE 1-continued

| Ex. No. | Name | Structure | LC/MS Rt Method M + H |
|---|---|---|---|
| 18 | (3S,4R)-4-(2,6-difluoro-4-methoxyphenyl)-3-[(5-{4-[(trifluoromethyl)sulfanyl]phenyl}-1,3,4-oxadiazol-2-yl)amino]pyrrolidin-2-one | 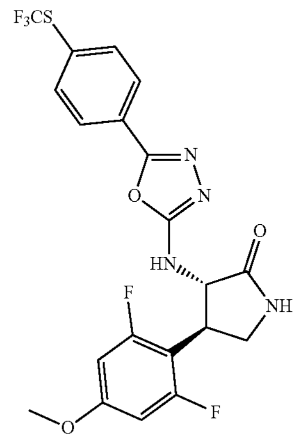 | 1.85 min (Method 1) 486.8 |
| 19 | (3S,4R)-4-(2,6-difluoro-4-methoxyphenyl)-3-[(5-{4-[(1,1,2,2,2-pentafluoroethyl)sulfanyl]phenyl}-1,3,4-oxadiazol-2-yl)amino]pyrrolidin-2-one | 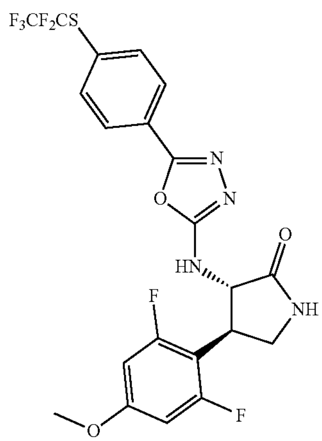 | 2.04 min (Method 1) 537 |
| 20 | (3S,4R)-3-{[5-(4-chlorophenyl)-1,3,4-oxadiazol-2-yl]amino}-4-(2,6-difluoro-4-methoxyphenyl)-1-methylpyrrolidin-2-one | 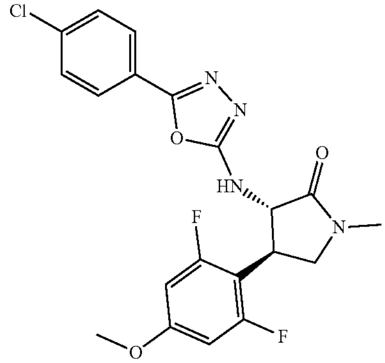 [SMILES: COc1cc(F)c([C@@H]2CN(C)C(=O)[C@H]2Nc2nnc(-c3ccc(Cl)cc3)o2)c(F)c1] | 1.67 min (Method 1) 434.8 |

TABLE 1-continued

| Ex. No. | Name | Structure | LC/MS Rt Method M + H |
|---|---|---|---|
| 22 | (3S,4R)-4-(2,6-difluoro-4-methoxyphenyl)-3-({5-[4-(difluoromethyl)phenyl]-1,2-oxazol-3-yl}amino)pyrrolidin-2-one | 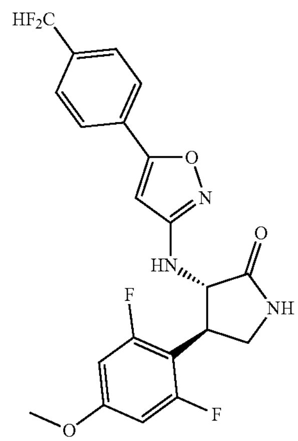 | 1.63 min (Method 1) 436.1 |
| 23 | (3S,4R)-4-(2,6-difluoro-4-methoxyphenyl)-3-({5-[4-(trifluoromethoxy)phenyl]-1,2-oxazol-3-yl}amino)pyrrolidin-2-one | 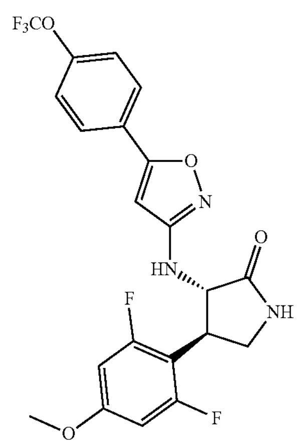 [SMILES: COc1cc(F)c([C@@H]2CNC(=O)[C@H]2Nc2cc(-c3ccc(OC(F)(F)F)cc3)on2)c(F)c1] | 1.92 min (Method 2) 470 |
| 26 | (3S,4R)-4-(2,6-difluoro-4-methoxyphenyl)-3-{[5-(4-trifluoromethanesulfinylphenyl)-1,3,4-oxadiazol-2-yl]amino}pyrrolidin-2-one | 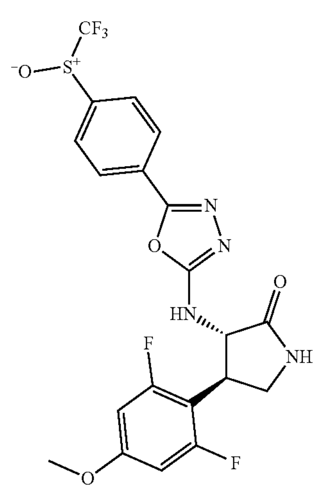 | 1.47 min (Method 1) 502.8 |

TABLE 1-continued

| Ex. No. | Name | Structure | LC/MS Rt Method M + H |
|---|---|---|---|
| 27 | (3S,4R)-4-(2,6-difluoro-4-methoxyphenyl)-3-[(5-{4-[(difluoromethyl)sulfanyl]phenyl}-1,3,4-oxadiazol-2-yl)amino]pyrrolidin-2-one | 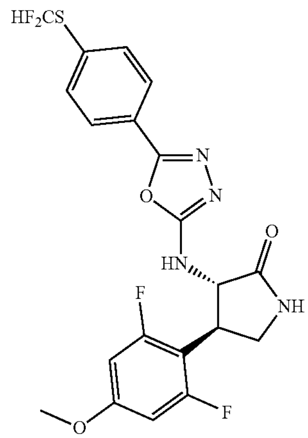 | 1.55 min (Method 2) 469.2 |
| 28 | (3S,4R)-4-(2,6-difluoro-4-methoxyphenyl)-3-[(5-{6-[(trifluoromethyl)sulfanyl]pyridin-3-yl}-1,3,4-oxadiazol-2-yl)amino]pyrrolidin-2-one | 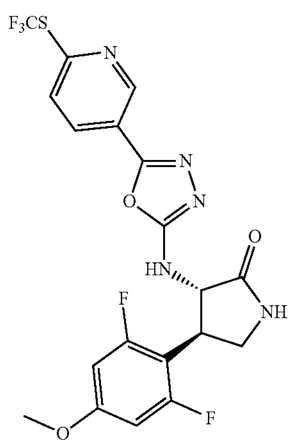 | 1.53 min (Method 2) 487.8 |
| 31 | (3S,4R)-3-{[5-(6-chloropyridin-3-yl)-1,3,4-thiadiazol-2-yl]amino}-4-(2,6-difluoro-4-methoxyphenyl)pyrrolidin-2-one | 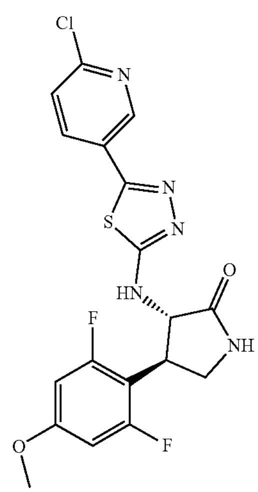 [SMILES: COc1cc(F)c([C@@H]2CNC(=O)[C@H]2Nc2nnc(-c3ccc(Cl)nc3)s2)c(F)c1] | 1.44 min (Method 1) 438.2 |

TABLE 1-continued

| Ex. No. | Name | Structure | LC/MS Rt Method M + H |
|---|---|---|---|
| 32 | (3S,4R)-4-(2,6-difluoro-4-methoxyphenyl)-3-{[5-(4-fluorophenyl)-1,3,4-thiadiazol-2-yl]amino}pyrrolidin-2-one | 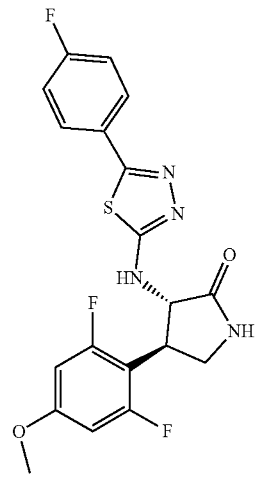 [SMILES: COc1cc(F)c([C@@H]2CNC(=O)[C@H]2Nc2nnc(-c3ccc(F)cc3)s2)c(F)c1] | 1.54 min (Method 1) 421.1 |
| 33 | (3S,4R)-4-(2,6-difluoro-4-methoxyphenyl)-3-({5-[6-(trifluoromethyl)pyridin-3-yl]-1,3,4-thiadiazol-2-yl}amino)pyrrolidin-2-one | 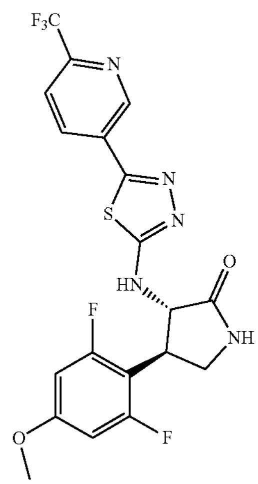 [SMILES: COc1cc(F)c([C@@H]2CNC(=O)[C@H]2Nc2nnc(-c3ccc(C(F)(F)F)nc3)s2)c(F)c1] | 1.6 min (Method 1) 472.2 |
| 36 | (3S,4R)-4-(2,6-difluoro-4-methoxyphenyl)-3-({5-[4-(propan-2-yloxy)phenyl]-1,3,4-oxadiazol-2-yl}amino)pyrrolidin-2-one | 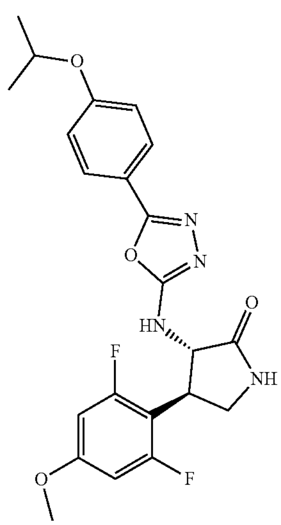 [SMILES: COc1cc(F)c([C@@H]2CNC(=O)[C@H]2Nc2nnc(-c3ccc(OC(C)C)cc3)o2)c(F)c1] | 1.66 min (Method 1) 445.1 |

TABLE 1-continued

| Ex. No. | Name | Structure | LC/MS Rt Method M + H |
|---|---|---|---|
| 37 | (3S,4R)-4-(2,6-difluoro-4-methoxyphenyl)-3-({5-[4-(difluoromethoxy)phenyl]-1,3,4-oxadiazol-2-yl}amino)pyrrolidin-2-one | 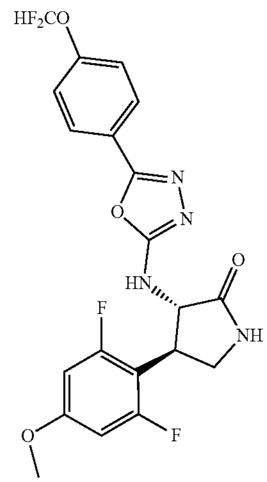 | 1.44 min (Method 2) 453 |
| 39 | (3S,4R)-4-(2,6-difluoro-4-methoxyphenyl)-3-({5-[4-(propan-2-yl)phenyl]-1,3,4-oxadiazol-2-yl}amino)pyrrolidin-2-one | 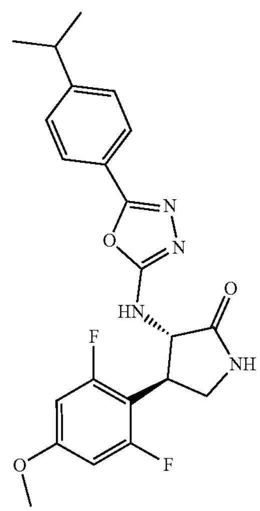 [SMILES: COc1cc(F)c([C@@H]2CNC(=O)[C@H]2Nc2nnc(-c3ccc(C(C)C)cc3)o2)c(F)c1] | 1.75 min (Method 1) 428.9 |
| 40 | (3S,4R)-3-({5-[4-(4-chlorophenoxy)phenyl]-1,3,4-oxadiazol-2-yl}amino)-4-(2,6-difluoro-4-methoxyphenyl)pyrrolidin-2-one | 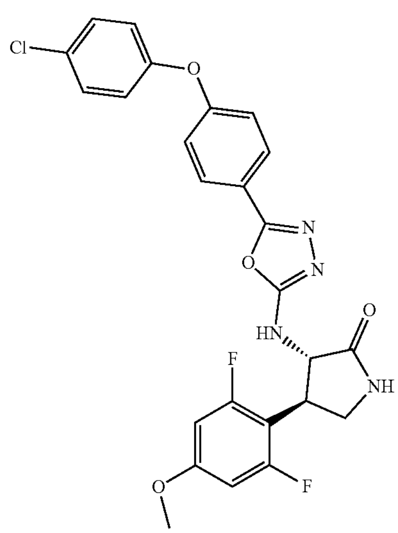 [SMILES: COc1cc(F)c([C@@H]2CNC(=O)[C@H]2Nc2nnc(-c3ccc(Oc4ccc(Cl)cc4)cc3)o2)c(F)c1] | 1.95 min (Method 2) 513 |

TABLE 1-continued

| Ex. No. | Name | Structure | LC/MS Rt Method M + H |
|---|---|---|---|
| 41 | (3S,4R)-3-({5-[2-(4-chlorophenyl)cyclopropyl]-1,3,4-oxadiazol-2-yl}amino)-4-(2,6-difluoro-4-methoxyphenyl)pyrrolidin-2-one | 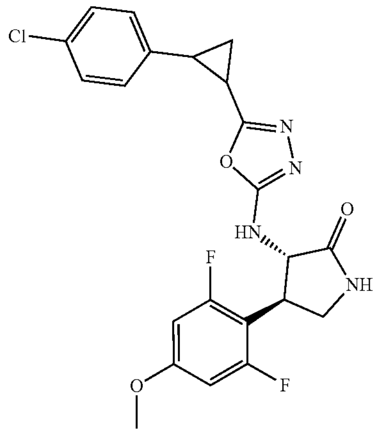 [SMILES: COc1cc(F)c([C@@H]2CNC(=O)[C@H]2Nc2nnc(C3CC3c3ccc(Cl)cc3)o2)c(F)c1] | 1.71 min (Method 1) 461.2 |
| 42 | (3S,4R)-4-(2,6-difluoro-4-methoxyphenyl)-3-({5-[2-(3,5-difluorophenyl)cyclopropyl]-1,3,4-oxadiazol-2-yl}amino)pyrrolidin-2-one | 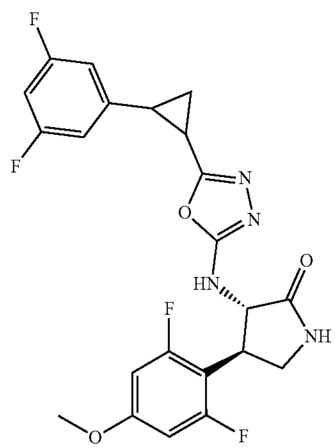 [SMILES: COc1cc(F)c([C@@H]2CNC(=O)[C@H]2Nc2nnc(C3CC3c3cc(F)cc(F)c3)o2)c(F)c1] | 1.63 min (Method 1) 463.2 |
| 43 | (3S,4R)-3-({5-[2-(4-chlorophenyl)cyclopropyl]-1,3,4-oxadiazol-2-yl}amino)-4-(2,6-difluoro-4-methoxyphenyl)pyrrolidin-2-one | 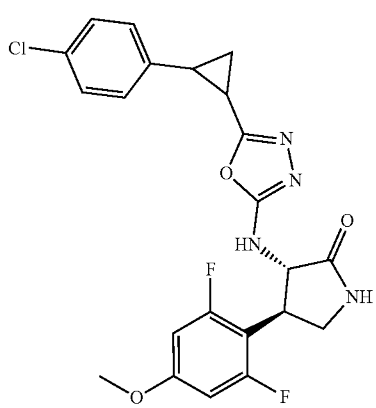 [SMILES: COc1cc(F)c([C@@H]2CNC(=O)[C@H]2Nc2nnc(C3CC3c3ccc(Cl)cc3)o2)c(F)c1] | 1.71 min (Method 1) 461 |

TABLE 1-continued

| Ex. No. | Name | Structure | LC/MS Rt Method M + H |
|---|---|---|---|
| 44 | (3S,4R)-4-(2,6-difluoro-4-methoxyphenyl)-3-({5-[2-(2-methoxyphenyl)cyclopropyl]-1,3,4-oxadiazol-2-yl}amino)pyrrolidin-2-one | 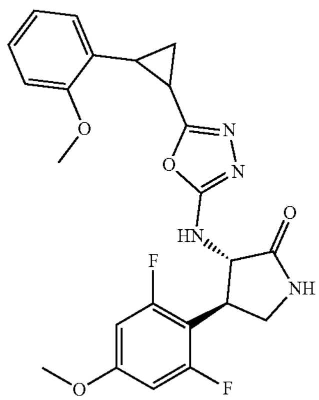 [SMILES: COc1cc(F)c([C@@H]2CNC(=O)[C@H]2Nc2nnc(C3CC3c3ccccc3OC)o2)c(F)c1] | 1.53 min (Method 2) 457.2 |
| 45 | (3S,4R)-3-({5-[2-(3-chlorophenyl)cyclopropyl]-1,3,4-oxadiazol-2-yl}amino)-4-(2,6-difluoro-4-methoxyphenyl)pyrrolidin-2-one | 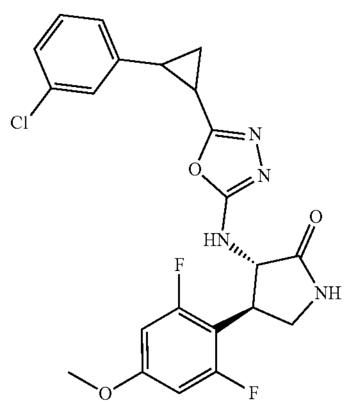 [SMILES: COc1cc(F)c([C@@H]2CNC(=O)[C@H]2Nc2nnc(C3CC3c3cccc(Cl)c3)o2)c(F)c1] | 1.69 min (Method 1) 461 |
| 46 | (3S,4R)-3-({5-[2-(4-chloro-2-fluorophenyl)cyclopropyl]-1,3,4-oxadiazol-2-yl}amino)-4-(2,6-difluoro-4-methoxyphenyl)pyrrolidin-2-one | 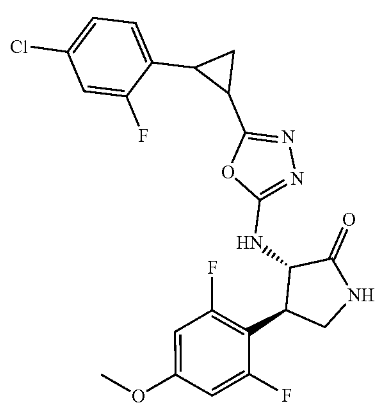 [SMILES: COc1cc(F)c([C@@H]2CNC(=O)[C@H]2Nc2nnc(C3CC3c3ccc(Cl)cc3F)o2)c(F)c1] | 1.81 min (Method 1) 479 |

TABLE 1-continued

| Ex. No. | Name | Structure | LC/MS Rt Method M + H |
|---|---|---|---|
| 48 | 2-[4-(5-{[(3S,4R)-4-(2,6-difluoro-4-methoxyphenyl)-2-oxopyrrolidin-3-yl]amino}-1,3,4-oxadiazol-2-yl)phenoxy]pyridine-4-carbonitrile | 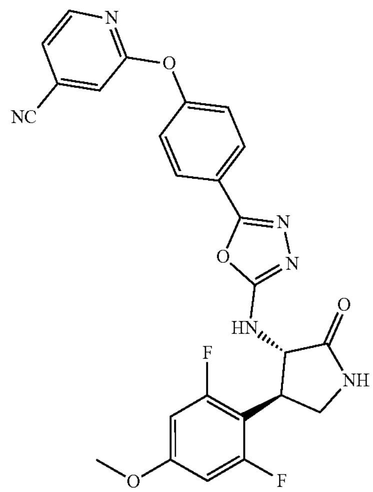 [SMILES: COc1cc(F)c([C@@H]2CNC(=O)[C@H]2Nc2nnc(-c3ccc(Oc4cc(C#N)ccn4)cc3)o2)c(F)c1] | 1.52 min (Method 1) 505 |
| 49 | (3S,4R)-4-(2,6-difluoro-4-methoxyphenyl)-3-({5-[4-(pyrazin-2-yloxy)phenyl]-1,3,4-oxadiazol-2-yl}amino)pyrrolidin-2-one | 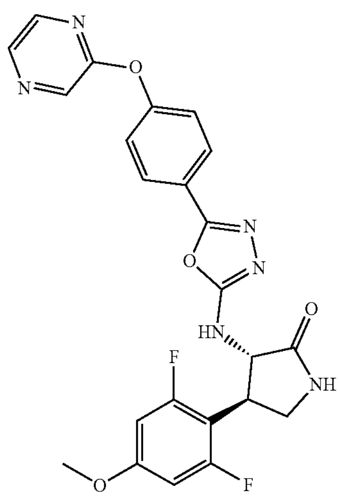 [SMILES: COc1cc(F)c([C@@H]2CNC(=O)[C@H]2Nc2nnc(-c3ccc(Oc4cnccn4)cc3)o2)c(F)c1] | 1.34 min (Method 1) 481 |
| 51 | (3S,4R)-3-({6-chloro-[1,2]oxazolo[4,5-b]pyridin-3-yl}amino)-4-(2,6-difluoro-4-methoxyphenyl)pyrrolidin-2-one | 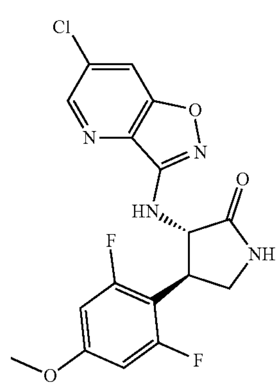 [SMILES: COc1cc(F)c([C@@H]2CNC(=O)[C@H]2Nc2noc3cc(Cl)cnc23)c(F)c1] | 1.51 min (Method 2) 395 |

TABLE 1-continued

| Ex. No. | Name | Structure | LC/MS Rt Method M + H |
|---|---|---|---|
| 54 | N-[2-(4-chlorophenyl)ethyl]-5-{[(3S,4R)-4-(2,6-difluoro-4-methoxyphenyl)-2-oxopyrrolidin-3-yl]amino}-1,3,4-oxadiazole-2-carboxamide | 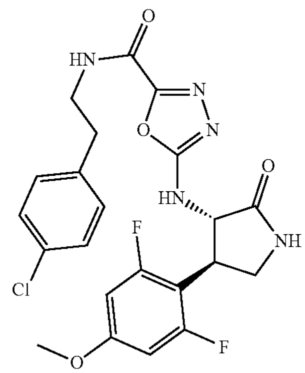 [SMILES: COc1cc(F)c([C@@H]2CNC(=O)[C@H]2Nc2nnc(C(=O)NCCc3ccc(Cl)cc3)o2)c(F)c1] | 1.53 min (Method 1) 492.2 |
| 56 | 6-[4-(5-{[(3S,4R)-4-(2,6-difluoro-4-methoxyphenyl)-2-oxopyrrolidin-3-yl]amino}-1,3,4-oxadiazol-2-yl)phenoxy]pyridine-3-carbonitrile | 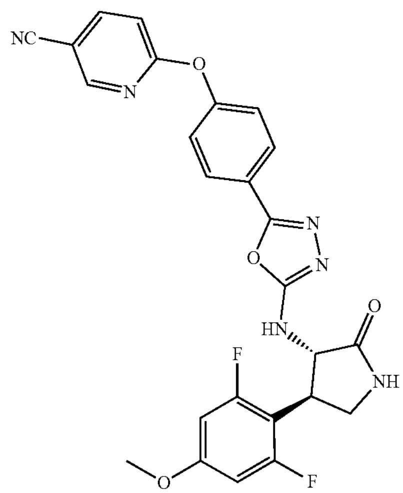 [SMILES: COc1cc(F)c([C@@H]2CNC(=O)[C@H]2Nc2nnc(-c3ccc(Oc4ccc(C#N)cn4)cc3)o2)c(F)c1] | 1.47 min (Method 2) 505.1 |
| 57 | 4-[4-(5-{[(3S,4R)-4-(2,6-difluoro-4-methoxyphenyl)-2-oxopyrrolidin-3-yl]amino}-1,3,4-oxadiazol-2-yl)phenoxy]benzonitrile | 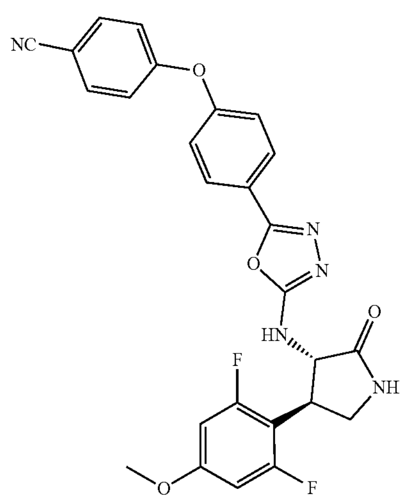 [SMILES: COc1cc(F)c([C@@H]2CNC(=O)[C@H]2Nc2nnc(-c3ccc(Oc4ccc(C#N)cc4)cc3)o2)c(F)c1] | 1.81 min (Method 1) 504 |

TABLE 1-continued

| Ex. No. | Name | Structure | LC/MS Rt Method M + H |
|---|---|---|---|
| 58 | (3S,4R)-4-(2,6-difluoro-4-methoxyphenyl)-3-{[5-(4-{[6-(trifluoromethyl)pyridin-3-yl]oxy}phenyl)-1,3,4-oxadiazol-2-yl]amino}pyrrolidin-2-one | 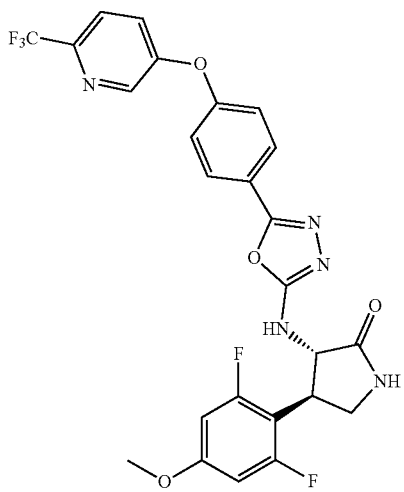 [SMILES: COc1cc(F)c([C@@H]2CNC(=O)[C@H]2Nc2nnc(-c3ccc(Oc4ccc(C(F)(F)F)nc4)cc3)o2)c(F)c1] | 1.82 min (Method 2) 548.3 |
| 59 | 6-[4-(5-{[(3S,4R)-4-(2,6-difluoro-4-methoxyphenyl)-2-oxopyrrolidin-3-yl]amino}-1,3,4-oxadiazol-2-yl)phenoxy]pyridine-2-carbonitrile | 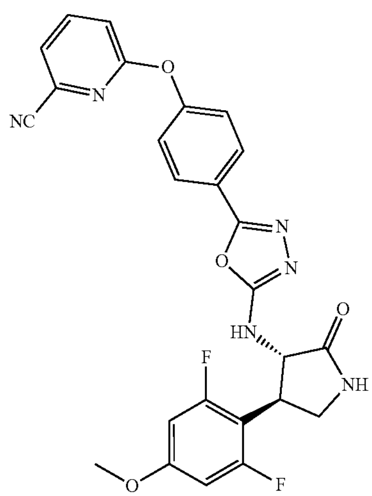 [SMILES: COc1cc(F)c([C@@H]2CNC(=O)[C@H]2Nc2nnc(-c3ccc(Oc4cccc(C#N)n4)cc3)o2)c(F)c1] | 1.53 min (Method 2) 504.9 |
| 60 | (3S,4R)-3-[(5-{4-[(5-chloropyrazin-2-yl)oxy]phenyl}-1,3,4-oxadiazol-2-yl)amino]-4-(2,6-difluoro-4-methoxyphenyl)pyrrolidin-2-one | 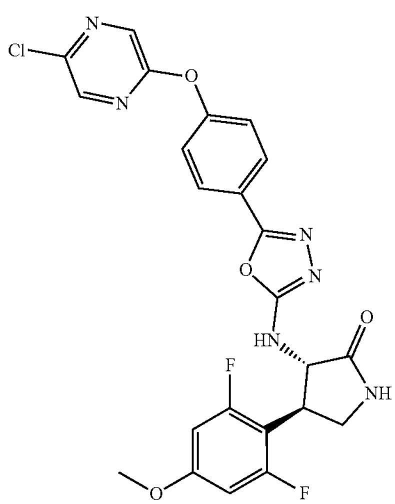 [SMILES: COc1cc(F)c([C@@H]2CNC(=O)[C@H]2Nc2nnc(-c3ccc(Oc4cnc(Cl)cn4)cc3)o2)c(F)c1] | 1.64 min (Method 2) 515.1 |

TABLE 1-continued

| Ex. No. | Name | Structure | LC/MS Rt Method M + H |
|---|---|---|---|
| 61 | (3S,4R)-4-(2,6-difluoro-4-methoxyphenyl)-3-[(5-{4-[(3-fluoropyridin-2-yl)oxy]phenyl}-1,3,4-oxadiazol-2-yl)amino]pyrrolidin-2-one | 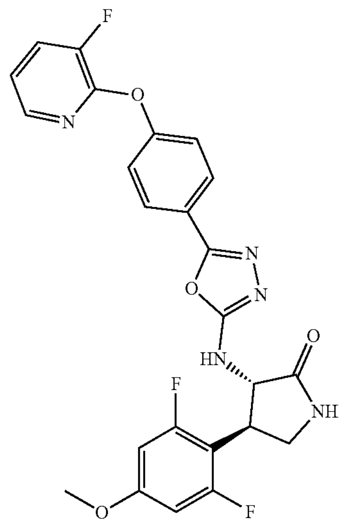 [SMILES: COc1cc(F)c([C@@H]2CNC(=O)[C@H]2Nc2nnc(-c3ccc(Oc4ncccc4F)cc3)o2)c(F)c1] | 1.53 min (Method 2) 498.3 |
| 62 | (3S,4R)-4-(2,6-difluoro-4-methoxyphenyl)-3-[(5-{4-[(6-methoxypyrimidin-4-yl)oxy]phenyl}-1,3,4-oxadiazol-2-yl)amino]pyrrolidin-2-one | 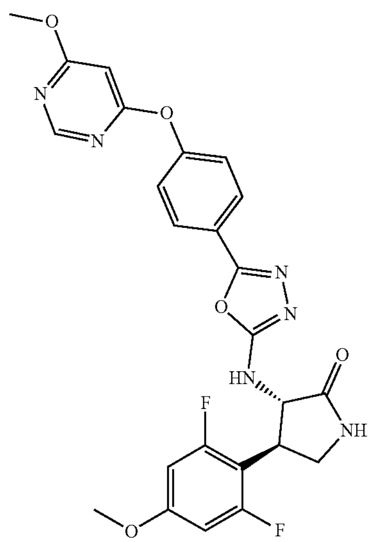 [SMILES: COc1cc(F)c([C@@H]2CNC(=O)[C@H]2Nc2nnc(-c3ccc(Oc4cc(OC)ncn4)cc3)o2)c(F)c1] | 1.48 min (Method 2) 511 |
| 63 | (3S,4R)-4-(2,6-difluoro-4-methoxyphenyl)-3-[(5-{4-[(6-methylpyrazin-2-yl)oxy]phenyl}-1,3,4-oxadiazol-2-yl)amino]pyrrolidin-2-one | 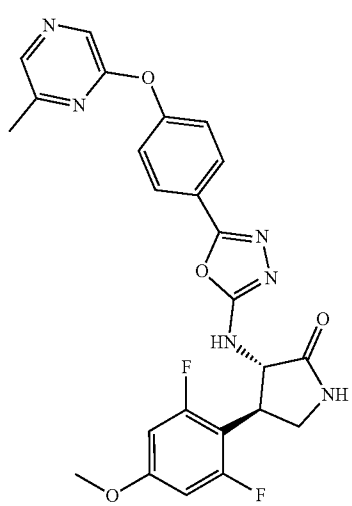 [SMILES: COc1cc(F)c([C@@H]2CNC(=O)[C@H]2Nc2nnc(-c3ccc(Oc4cncc(C)n4)cc3)o2)c(F)c1] | 1.53 min (Method 1) 495.3 |

TABLE 1-continued

| Ex. No. | Name | Structure | LC/MS Rt Method M + H |
|---|---|---|---|
| 64 | (3S,4R)-4-(2,6-difluoro-4-methoxyphenyl)-3-[(5-{4-[(6-fluoropyridin-2-yl)oxy]phenyl}-1,3,4-oxadiazol-2-yl)amino]pyrrolidin-2-one | 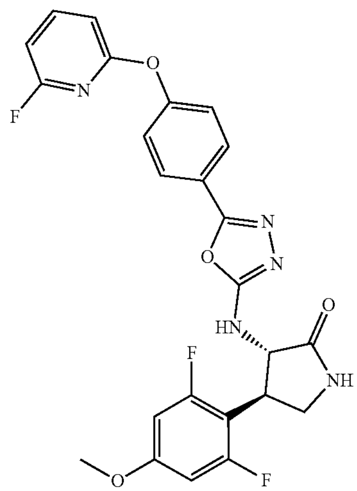 [SMILES: COc1cc(F)c([C@@H]2CNC(=O)[C@H]2Nc2nnc(-c3ccc(Oc4cccc(F)n4)cc3)o2)c(F)c1] | 1.58 min (Method 2) 498.2 |
| 65 | (3S,4R)-4-(2,6-difluoro-4-methoxyphenyl)-3-[(5-{4-[(5-fluoropyridin-2-yl)oxy]phenyl}-1,3,4-oxadiazol-2-yl)amino]pyrrolidin-2-one | 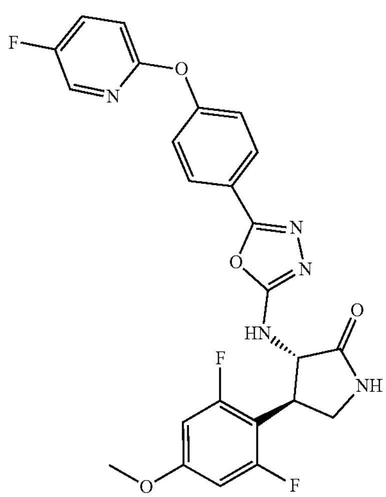 [SMILES: COc1cc(F)c([C@@H]2CNC(=O)[C@H]2Nc2nnc(-c3ccc(Oc4ccc(F)cn4)cc3)o2)c(F)c1] | 1.53 min (Method 2) 498.1 |
| 66 | 2-[4-(5-{[(3S,4R)-4-(2,6-difluoro-4-methoxyphenyl)-2-oxopyrrolidin-3-yl]amino}-1,3,4-oxadiazol-2-yl)phenoxy]pyridine-3-carbonitrile | 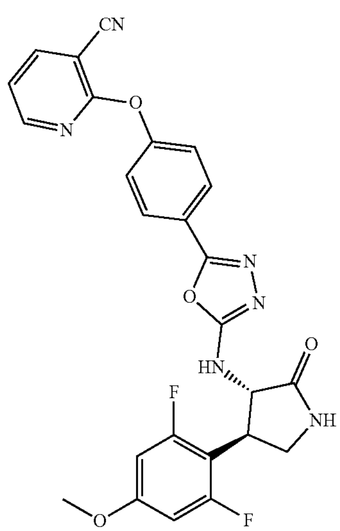 [SMILES: COc1cc(F)c([C@@H]2CNC(=O)[C@H]2Nc2nnc(-c3ccc(Oc4ncccc4C#N)cc3)o2)c(F)c1] | 1.44 min (Method 2) 505.2 |

| Ex. No. | Name | Structure | LC/MS Rt Method M + H |
|---|---|---|---|
| 67 | (3S,4R)-4-(2,6-difluoro-4-methoxyphenyl)-3-[(5-{4-[(6-methoxypyridin-2-yl)oxy]phenyl}-1,3,4-oxadiazol-2-yl)amino]pyrrolidin-2-one | 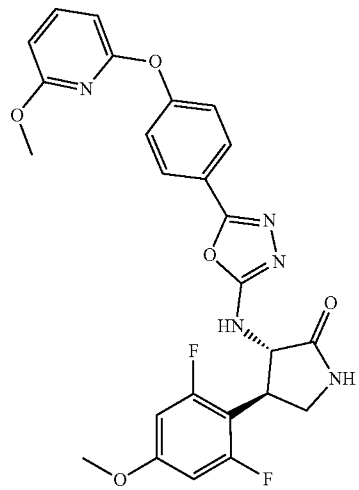 [SMILES: COc1cc(F)c([C@@H]2CNC(=O)[C@H]2Nc2nnc(-c3ccc(Oc4cccc(OC)n4)cc3)o2)c(F)c1] | 1.72 min (Method 2) 510.1 |
| 68 | (3S,4R)-3-[(5-{4-[(4-chloropyridin-2-yl)oxy]phenyl}-1,3,4-oxadiazol-2-yl)amino]-4-(2,6-difluoro-4-methoxyphenyl)pyrrolidin-2-one | 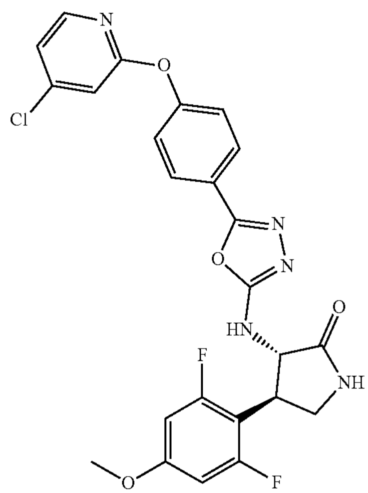 [SMILES: COc1cc(F)c([C@@H]2CNC(=O)[C@H]2Nc2nnc(-c3ccc(Oc4cc(Cl)ccn4)cc3)o2)c(F)c1] | 1.73 min (Method 1) 514.2 |

¹H NMR data for Examples in Table 1:

Example 2

¹H NMR (500 MHz, DMSO-d₆) δ 8.41 (br d, J=7.9 Hz, 1H), 8.20 (br s, 1H), 7.73 (br d, J=8.3 Hz, 2H), 7.52 (br d, J=8.4 Hz, 2H), 6.74 (br d, J=10.9 Hz, 2H), 4.77-4.61 (m, 1H), 4.03 (q, J=9.4 Hz, 1H), 3.87 (s, 3H), 3.54 (br t, J=9.1 Hz, 1H), 3.37 (br t, J=9.6 Hz, 1H).

Example 4

¹H NMR (500 MHz, DMSO-d₆) δ 8.29 (d, J=8.8 Hz, 1H), 8.23 (s, 1H), 7.76 (d, J=3.7 Hz, 2H), 7.52 (br. s., 3H), 6.75 (d, J=10.7 Hz, 2H), 4.52 (t, J=9.9 Hz, 1H), 4.05-3.93 (m, 1H), 3.74 (s, 3H), 3.57 (d, J=5.8 Hz, 1H), 3.39 (t, J=9.6 Hz, 1H).

Example 5

¹H NMR (500 MHz, DMSO-d₆) δ 8.37 (d, J=8.2 Hz, 1H), 8.25 (s, 1H), 7.81-7.71 (m, 1H), 7.61 (d, J=2.7 Hz, 2H), 6.76 (d, J=10.7 Hz, 2H), 4.61-4.49 (m, 1H), 4.08-3.93 (m, 1H), 3.81-3.70 (m, 3H), 3.42-3.34 (m, 2H)

Example 6

¹H NMR (500 MHz, DMSO-d₆) δ 8.93 (s, 1H), 8.69 (d, J=4.5 Hz, 1H), 8.44 (d, J=7.6 Hz, 1H), 8.28 (s, 1H), 8.12 (d, J=8.0 Hz, 1H), 7.56 (dd, J=7.9, 4.9 Hz, 1H), 6.76 (d, J=10.5 Hz, 2H), 4.59-4.48 (m, 1H), 3.98 (q, J=9.6 Hz, 1H), 3.74 (s, 3H), 3.42-3.35 (m, 2H)

Example 7

¹H NMR (500 MHz, DMSO-d₆) δ 8.36 (d, J=8.5 Hz, 1H), 8.25 (s, 1H), 7.88 (d, J=8.9 Hz, 2H), 7.53 (d, J=8.2 Hz, 2H), 6.76 (d, J=10.7 Hz, 2H), 4.58-4.51 (m, 1H), 4.05-3.93 (m, 1H), 3.74 (s, 3H), 3.43-3.33 (m, 2H)

Example 8

¹H NMR (500 MHz, DMSO-d₆) δ 8.46 (d, J=8.5 Hz, 1H), 8.27 (s, 1H), 8.01-7.86 (m, 4H), 6.76 (d, J=10.7 Hz, 2H), 4.64-4.49 (m, 1H), 3.98 (q, J=9.5 Hz, 1H), 3.74 (s, 3H), 3.44 (m, 2H)

Example 9

¹H NMR (500 MHz, DMSO-d₆) δ 8.53 (d, J=9.4 Hz, 1H), 8.30 (s, 1H), 8.03-7.87 (m, 4H), 6.77 (d, J=10.9 Hz, 2H), 4.55 (d, J=9.3 Hz, 1H), 3.97 (d, J=10.4 Hz, 1H), 3.74 (s, 3H), 3.45 (m, 2H)

Example 10

¹H NMR (500 MHz, DMSO-d₆) δ 9.10 (s, 1H), 8.60 (bd, J=7.3 Hz, 1H), 8.38 (bd, J=8.0 Hz, 1H), 8.31 (s, 1H), 8.06 (d, J=8.2 Hz, 1H), 6.77 (d, J=10.9 Hz, 2H), 4.66-4.54 (m, 1H), 4.06-3.93 (m, 1H), 3.74 (s, 3H), 3.55 (m, 2H)

Example 11

¹H NMR (500 MHz, DMSO-d₆) δ 8.27-8.18 (m, 2H), 7.65 (d, J=7.9 Hz, 2H), 7.33 (d, J=8.2 Hz, 2H), 6.75 (d, J=11.0 Hz, 2H), 4.51 (t, J=9.9 Hz, 1H), 3.99 (q, J=9.6 Hz, 1H), 3.74 (s, 3H), 3.53 (m, 1H), 3.38 (t, J=9.6 Hz, 1H), 2.35 (s, 3H)

Example 12

¹H NMR (500 MHz, DMSO-d₆) δ 8.33 (d, J=8.2 Hz, 1H), 8.25 (s, 1H), 7.81 (dd, 5.4 Hz, 2H), 7.36 (t, J=8.6 Hz, 2H), 6.75 (d, J=10.9 Hz, 2H), 4.57-4.47 (m, 1H), 3.98 (d, J=10.2 Hz, 1H), 3.63 (s, 3H), 3.38 (t, J=9.8 Hz, 1H)

Example 13

¹H NMR (500 MHz, DMSO-d₆) δ 8.53 (d, J=2.1 Hz, 1H), 8.33 (d, J=8.9 Hz, 1H), 8.23 (s, 1H), 8.05-7.84 (m, 4H), 7.80 (s, 1H), 6.75 (bd, J=11.0 Hz, 2H), 6.59 (s, 1H), 4.60-4.41 (m, 1H), 4.06-3.93 (m, 1H), 3.73 (s, 3H), 3.39 (t, J=9.8 Hz, 1H), 3.17 (m, 1H)

Example 14

¹H NMR (500 MHz, DMSO-d₆) δ 9.08 (s, 1H), 8.61 (d, J=9.2 Hz, 1H), 8.37 (d, J=8.5 Hz, 1H), 8.29 (s, 1H), 8.14 (d, J=8.5 Hz, 1H), 6.78 (d, J=11.0 Hz, 2H), 4.57 (t, J=9.9 Hz, 1H), 4.09-3.93 (m, 1H), 3.75 (s, 3H), 3.56 (t, J=8.7 Hz, 1H)

Example 15

¹H NMR (500 MHz, DMSO-d₆) δ 8.42 (d, J=9.2 Hz, 1H), 8.25 (s, 1H), 7.81 (t, J=8.1 Hz, 1H), 7.66 (d, J=9.2 Hz, 1H), 7.46 (d, J=8.5 Hz, 1H), 6.76 (d, J=10.7 Hz, 2H), 4.57-4.46 (m, 1H), 4.05-3.93 (m, 1H), 3.74 (s, 3H), 3.52-3.33 (m, 2H)

Example 16

¹H NMR (500 MHz, DMSO-d₆) δ 8.74 (d, J=2.1 Hz, 1H), 8.50 (d, J=8.2 Hz, 1H), 8.25 (s, 1H), 8.16 (dd, J=8.4, 2.3 Hz, 1H), 7.66 (d, J=8.4 Hz, 1H), 6.73 (d, J=10.8 Hz, 2H), 4.65-4.49 (m, 1H), 3.99-3.95 (m, 1H), 3.75 (s, 3H), 3.53 (t, J=9.2 Hz, 1H), 3.38 (t, J=9.6 Hz, 1H)

Example 17

¹H NMR (500 MHz, DMSO-d₆) δ 8.43 (d, J=8.2 Hz, 1H), 8.28 (s, 1H), 7.95-7.68 (m, 4H), 7.08 (t, J=53.3 Hz, 1H), 6.76 (d, J=10.9 Hz, 2H), 4.65-4.46 (m, 1H), 3.98 (q, J=9.6 Hz, 1H), 3.73 (s, 3H), 3.53 (m, 1H), 3.39 (t, J=9.6 Hz, 1H)

Example 18

¹H NMR (500 MHz, DMSO-d₆) δ 8.48 (d, J=8.6 Hz, 1H), 8.28 (s, 1H), 7.94-7.81 (m, 4H), 6.76 (d, J=10.9 Hz, 2H), 4.54 (t, J=9.8 Hz, 1H), 4.09-3.89 (m, 1H), 3.72 (s, 3H), 3.66 (m, 1H), 3.39 (t, J=9.6 Hz, 1H)

Example 19

¹H NMR (500 MHz, DMSO-d₆) δ 8.47 (d, J=8.5 Hz, 1H), 8.30 (s, 1H), 7.96-7.83 (m, 4H), 6.78 (d, J=10.9 Hz, 2H), 4.61-4.50 (m, 1H), 3.97 (d, J=10.4 Hz, 1H), 3.84-3.70 (m, 4H), 3.55 (t, J=8.8 Hz, 1H)

Example 20

¹H NMR (500 MHz, DMSO-d₆) δ 8.40 (d, J=8.9 Hz, 1H), 7.76 (d, J=8.5 Hz, 2H), 7.58 (bd, J=8.2 Hz, 2H), 6.74 (d, J=10.7 Hz, 2H), 4.66 (d, J=8.5 Hz, 1H), 4.58-4.50 (m, 1H), 3.76-3.71 (m, 3H), 3.74 (s, 3H), 3.26 (dt, J=10.8, 5.5 Hz, 1H), 3.19-3.13 (m, 1H).

Example 22

¹H NMR (500 MHz, DMSO-d₆) δ 8.18 (s, 1H), 7.98 (d, J=8.9 Hz, 1H), 7.60-7.48 (m, 4H), 7.32 (s, 1H), 7.00 (t, J=56.2 Hz, 1H), 6.76 (d, J=10.7 Hz, 2H), 4.55 (t, J=9.9 Hz, 1H), 3.98 (q, J=10.0 Hz, 1H), 3.74 (s, 3H), 3.52 (t, J=8.9 Hz, 1H), 3.40-3.35 (m, 1H).

Example 23

¹H NMR (500 MHz, DMSO-d₆) δ 8.09 (s, 1H), 7.87 (d, J=8.5 Hz, 2H), 7.48 (d, J=8.2 Hz, 2H), 6.82-6.67 (m, 3H), 6.45 (s, 1H), 4.42-4.34 (m, 1H), 3.97 (q, J=9.7 Hz, 1H), 3.76 (s, 3H), 3.61-3.55 (m, 1H), 3.54-3.46 (m, 1H).

Example 26

¹H NMR (500 MHz, DMSO-d₆) δ 8.50 (d, J=8.9 Hz, 1H), 8.27 (s, 1H), 8.10-7.98 (m, 4H), 6.77 (d, J=11.0 Hz, 2H), 4.62-4.52 (m, 1H), 4.03-3.90 (m, 1H), 3.79 (s, 3H), 3.59-3.32 (m, 2H)

Example 27

¹H NMR (500 MHz, DMSO-d₆) δ 8.40 (d, J=8.9 Hz, 1H), 8.23 (s, 1H), 7.85-7.68 (m, 4H), 7.52 (t, J=57.4 Hz, 1H), 6.74 (d, J=11.0 Hz, 2H), 4.53 (t, J=9.9 Hz, 1H), 4.04-3.94 (m, 1H), 3.73 (s, 3H), 3.63 (m, 1H), 3.39 (t, J=9.5 Hz, 1H)

Example 28

¹H NMR (500 MHz, DMSO-d₆) δ 8.94 (s, 1H), 8.53 (d, J=8.9 Hz, 1H), 8.27-8.17 (m, 2H), 7.84 (d, J=8.2 Hz, 1H), 6.72 (d, J=10.7 Hz, 2H), 4.62-4.52 (m, 1H), 3.97 (m, 1H), 3.76 (s, 3H), 3.53 (m, 1H), 3.39 (t, J=9.6 Hz, 1H)

Example 31

¹H NMR (500 MHz, DMSO-d₆) δ 8.76 (s, 1H), 8.54 (d, J=8.2 Hz, 1H), 8.25 (s, 1H), 8.19 (dd, J=8.2, 1.8 Hz, 1H), 7.63 (d, J=8.5 Hz, 1H), 6.77 (d, J=10.7 Hz, 2H), 4.74 (t,

J=9.5 Hz, 1H), 4.03 (q, J=9.2 Hz, 1H), 3.77 (s, 3H), 3.56 (br t, J=9.3 Hz, 1H), 3.39 (br d, J=15.9 Hz, 1H).

Example 32

$^1$H NMR (500 MHz, DMSO-d$_6$) δ 8.35 (d, J=8.5 Hz, 1H), 8.21 (s, 1H), 7.78 (br dd, J=8.2, 5.5 Hz, 2H), 7.31 (t, J=8.7 Hz, 2H), 6.76 (d, J=11.0 Hz, 2H), 4.78-4.61 (m, 1H), 4.03 (q, J=9.6 Hz, 1H), 3.76 (s, 3H), 3.60-3.51 (m, 1H), 3.42-3.33 (m, 1H).

Example 33

$^1$H NMR (500 MHz, DMSO-d$_6$) δ 9.11 (s, 1H), 8.64 (d, J=8.2 Hz, 1H), 8.38 (d, J=7.9 Hz, 1H), 8.26 (s, 1H), 7.99 (d, J=8.2 Hz, 1H), 6.77 (d, J=11.0 Hz, 2H), 4.76 (dd, J=10.7, 8.5 Hz, 1H), 4.10-3.96 (m, 1H), 3.76 (s, 3H), 3.58 (d, J=8.2 Hz, 1H), 3.47 (d, J=4.0 Hz, 1H).

Example 36

$^1$H NMR (500 MHz, DMSO-d$_6$) δ 8.31-8.21 (m, 1H), 8.19 (d, J=8.8 Hz, 1H), 7.67 (d, J=8.7 Hz, 2H), 7.04 (d, J=8.7 Hz, 2H), 6.77 (br d, J=10.9 Hz, 2H), 4.69 (dt, J=12.0, 6.0 Hz, 1H), 4.55-4.44 (m, 1H), 3.98 (q, J=9.6 Hz, 1H), 3.74 (s, 3H), 3.48 (br s, 1H), 3.38 (br t, J=9.4 Hz, 1H), 1.29 (d, J=6.0 Hz, 6H)

Example 37

$^1$H NMR (500 MHz, DMSO-d$_6$) δ 8.30 (br d, J=8.9 Hz, 1H), 8.24 (s, 1H), 7.81 (br d, J=8.9 Hz, 2H), 7.33 (d, J=8.7 Hz, 2H), 7.32 (t, J=73.5 Hz, 1H), 6.76 (br d, J=10.7 Hz, 2H), 4.52 (br t, J=10.1 Hz, 1H), 3.99 (br d, J=10.1 Hz, 1H), 3.74 (s, 3H), 3.56-3.47 (m, 1H), 3.42-3.32 (m, 1H)

Example 39

$^1$H NMR (500 MHz, DMSO-d$_6$) δ 8.19 (s, 1H), 7.66 (br d, J=8.2 Hz, 2H), 7.38 (br d, J=8.2 Hz, 2H), 6.72 (br d, J=11.0 Hz, 2H), 4.56-4.46 (m, 1H), 4.04-3.93 (m, 1H), 3.71 (s, 3H), 3.53 (br t, J=9.0 Hz, 1H), 3.39 (br t, J=9.6 Hz, 1H), 2.92 (dt, J=13.7, 6.9 Hz, 1H), 1.19 (d, J=7.0 Hz, 6H)

Example 40

$^1$H NMR (500 MHz, DMSO-d$_6$) δ 8.16-8.07 (m, 2H), 7.77 (d, J=8.8 Hz, 2H), 7.48 (d, J=8.8 Hz, 2H), 7.14 (d, J=8.7 Hz, 4H), 6.74 (br d, J=10.7 Hz, 2H), 4.56-4.49 (m, 1H), 4.00 (d, J=10.1 Hz, 1H), 3.76 (s, 3H), 3.61-3.49 (m, 1H), 3.42-3.35 (m, 1H).

Example 41

$^1$H NMR (500 MHz, DMSO-d$_6$) δ 8.16 (s, 1H), 7.97-7.89 (m, 1H), 7.33 (br d, J=8.2 Hz, 2H), 7.22 (br dd, J=8.4, 3.2 Hz, 2H), 6.75 (br dd, J=10.7, 3.4 Hz, 2H), 4.46-4.35 (m, 1H), 3.94 (br d, J=11.0 Hz, 1H), 3.75 (s, 3H), 3.64-3.47 (m, 1H), 3.33 (br t, J=9.5 Hz, 1H), 2.46-2.22 (m, 2H), 1.49 (m, 2H)

Example 42

$^1$H NMR (500 MHz, DMSO-d$_6$) δ 8.19 (s, 1H), 7.94 (br dd, J=9.0, 2.6 Hz, 1H), 7.05-6.97 (m, 3H), 6.78 (br dd, J=10.7, 4.3 Hz, 2H), 4.49-4.35 (m, 1H), 4.04-3.92 (m, 1H), 3.77 (d, J=2.4 Hz, 3H), 3.61-3.52 (m, 1H), 3.32-3.23 (m, 1H), 2.48-2.40 (m, 2H), 1.63-1.46 (m, 2H)

Example 43

$^1$H NMR (500 MHz, DMSO-d$_6$) δ 8.05 (s, 1H), 7.80 (br d, J=8.9 Hz, 1H), 7.33 (d, J=8.3 Hz, 2H), 7.23 (dd, J=8.5, 2.9 Hz, 2H), 6.74 (br dd, J=10.6, 3.5 Hz, 2H), 4.48-4.37 (m, 1H), 3.96 (q, J=9.3 Hz, 1H), 3.77 (d, J=1.1 Hz, 3H), 3.65-3.56 (m, 1H), 3.51 (br t, J=9.0 Hz, 1H), 2.46-2.35 (m, 1H), 2.33-2.23 (m, 1H), 1.56-1.44 (m, 2H)

Example 44

$^1$H NMR (500 MHz, DMSO-d$_6$) δ 8.04 (s, 1H), 7.79 (br d, J=8.8 Hz, 1H), 7.25-7.15 (m, 1H), 7.03-6.94 (m, 2H), 6.93-6.84 (m, 1H), 6.73 (d, J=10.7 Hz, 2H), 4.41 (br t, J=9.3 Hz, 1H), 4.03-3.92 (m, 1H), 3.80 (s, 3H), 3.76 (s, 3H), 3.64-3.56 (m, 1H), 3.50 (br d, J=8.8 Hz, 1H), 2.50-2.46 (m, 1H), 2.22-2.15 (m, 1H), 1.49-1.39 (m, 2H)

Example 45

$^1$H NMR (500 MHz, DMSO-d$_6$) δ 8.04 (s, 1H), 7.80 (br d, J=8.8 Hz, 1H), 7.36-7.23 (m, 3H), 7.17 (br d, J=4.1 Hz, 1H), 6.74 (br dd, J=10.6, 4.1 Hz, 2H), 4.47-4.37 (m, 1H), 3.96 (q, J=9.8 Hz, 1H), 3.77 (d, J=2.1 Hz, 3H), 3.63-3.56 (m, 1H), 3.53-3.48 (m, 1H), 2.47-2.38 (m, 1H), 2.36-2.30 (m, 1H), 1.55-1.45 (m, 2H)

Example 46

$^1$H NMR (500 MHz, DMSO-d$_6$) δ 8.05 (s, 1H), 7.36 (br d, J=10.4 Hz, 1H), 7.27-7.19 (m, 2H), 6.73 (br d, J=10.7 Hz, 2H), 4.51-4.36 (m, 1H), 3.96 (q, J=9.6 Hz, 1H), 3.77 (d, J=1.9 Hz, 3H), 3.65-3.58 (m, 1H), 3.51 (br t, J=9.1 Hz, 1H), 2.49-2.41 (m, 1H), 2.39-2.32 (m, 1H), 1.59-1.46 (m, 2H)

Example 48

$^1$H NMR (500 MHz, DMSO-d$_6$) δ 8.44-8.38 (m, 1H), 8.13-8.09 (m, 1H), 7.86-7.76 (m, 2H), 7.68-7.63 (m, 1H), 7.63-7.56 (m, 1H), 7.33 (d, J=8.7 Hz, 2H), 6.77-6.70 (m, 2H), 4.58-4.51 (m, 1H), 4.06-3.96 (m, 1H), 3.76 (s, 3H), 3.55 (m, 1H), 3.43-3.36 (m, 1H).

Example 49

$^1$H NMR (500 MHz, DMSO-d$_6$) δ 8.58 (s, 1H), 8.43 (d, J=2.5 Hz, 1H), 8.25 (s, 1H), 8.11 (s, 1H), 7.82 (d, J=8.8 Hz, 2H), 7.36 (d, J=8.8 Hz, 2H), 6.74 (d, J=10.7 Hz, 2H), 4.57-4.49 (m, 1H), 4.05-3.96 (m, 1H), 3.76 (s, 3H), 3.61-3.51 (m, 1H), 3.46-3.34 (m, 1H).

Example 51

$^1$H NMR (500 MHz, DMSO-d$_6$) δ 8.60 (d, J=1.8 Hz, 1H), 8.24 (d, J=1.6 Hz, 1H), 8.01 (s, 1H), 7.46 (d, J=8.8 Hz, 1H), 6.71 (d, J=10.7 Hz, 2H), 4.85-4.67 (m, 1H), 4.28-4.14 (m, 1H), 3.76 (s, 3H), 3.54 (t, J=9.0 Hz, 1H), 3.39 (t, J=9.5 Hz, 1H).

Example 54

$^1$H NMR (500 MHz, DMSO-d$_6$) δ 8.93 (t, J=5.8 Hz, 1H), 8.27 (s, 1H), 7.33 (d, J=8.2 Hz, 2H), 7.24 (d, J=8.5 Hz, 2H), 6.76 (d, J=11.0 Hz, 2H), 4.50 (d, J=9.2 Hz, 1H), 4.00-3.91 (m, 1H), 3.77 (s, 3H), 3.53 (t, J=9.8 Hz, 1H), 3.47-3.36 (m, 3H), 2.80 (t, J=7.0 Hz, 2H).

Example 56

$^1$H NMR (500 MHz, DMSO-$d_6$) δ 8.66 (s, 1H), 8.40-8.29 (m, 2H), 8.24 (s, 1H), 7.83 (d, J=8.5 Hz, 2H), 7.36 (d, J=8.5 Hz, 2H), 7.31 (d, J=8.5 Hz, 1H), 6.76 (br d, J=11.0 Hz, 2H), 4.53 (br t, J=9.9 Hz, 1H), 3.99 (q, J=10.1 Hz, 1H), 3.74 (s, 3H), 3.57-3.47 (m, 1H), 3.39 (br t, J=9.3 Hz, 1H)

Example 57

$^1$H NMR (500 MHz, DMSO-$d_6$) δ 8.29 (d, J=8.9 Hz, 1H), 8.24 (s, 1H), 7.88 (d, J=8.5 Hz, 2H), 7.83 (d, J=8.5 Hz, 2H), 7.26 (d, J=8.5 Hz, 2H), 7.21 (d, J=8.5 Hz, 2H), 6.76 (d, J=10.7 Hz, 2H), 4.60-4.48 (m, 1H), 4.02-3.94 (m, 1H), 3.74 (s, 3H), 2.55 (m, 2H).

Example 58

$^1$H NMR (500 MHz, DMSO-$d_6$) δ 8.64 (s, 1H), 8.36-8.17 (m, 2H), 7.96 (d, J=8.5 Hz, 1H), 7.84 (d, J=8.5 Hz, 2H), 7.75-7.67 (m, 1H), 7.72 (d, J=8.5 Hz, 1H), 7.33 (d, J=8.5 Hz, 2H), 6.77 (d, J=11.0 Hz, 2H), 4.60-4.48 (m, 1H), 4.04-3.90 (m, 1H), 3.57-3.50 (m, 1H), 3.40-3.07 (m, 3H).

Example 59

$^1$H NMR (500 MHz, DMSO-$d_6$) δ 8.12 (t, J=7.9 Hz, 2H), 7.89-7.78 (m, 4H), 7.47 (d, J=8.5 Hz, 1H), 7.35 (d, J=8.8 Hz, 3H), 6.74 (br d, J=10.7 Hz, 1H), 4.54 (dd, J=10.8, 9.0 Hz, 1H), 4.06-3.96 (m, 1H), 3.76 (s, 3H), 3.63-3.51 (m, 2H).

Example 60

$^1$H NMR (500 MHz, DMSO-$d_6$) δ 8.46 (d, J=1.1 Hz, 1H), 8.43-8.35 (m, 1H), 7.83 (d, J=8.8 Hz, 3H), 7.39 (d, J=8.8 Hz, 3H), 6.75 (d, J=10.7 Hz, 2H), 4.59-4.49 (m, 1H), 4.08-3.96 (m, 1H), 3.77 (s, 3H), 3.59-3.51 (m, 1H), 3.45-3.34 (m, 1H).

Example 61

$^1$H NMR (500 MHz, DMSO-$d_6$) δ 8.35-7.97 (m, 2H), 7.80 (s, 3H), 7.32 (d, J=8.7 Hz, 2H), 7.14 (d, J=8.8 Hz, 1H), 6.74 (br dd, J=10.8, 2.1 Hz, 2H), 4.60-4.45 (m, 1H), 4.07-3.95 (m, 1H), 3.76 (d, J=2.6 Hz, 3H), 3.59-3.50 (m, 1H).

Example 62

$^1$H NMR (500 MHz, DMSO-$d_6$) δ 8.48 (s, 1H), 8.17 (br d, J=8.8 Hz, 1H), 8.11 (s, 1H), 7.82 (d, J=8.7 Hz, 2H), 7.34 (d, J=8.6 Hz, 2H), 6.74 (br d, J=10.7 Hz, 2H), 6.47 (s, 1H), 4.60-4.48 (m, 1H), 4.01 (br d, J=10.2 Hz, 1H), 3.98-3.94 (m, 3H), 3.76 (s, 3H), 3.63-3.55 (m, 1H), 3.44-3.35 (m, 1H)

Example 63

$^1$H NMR (500 MHz, DMSO-$d_6$) δ 8.33 (d, J=2.6 Hz, 2H), 8.18-8.07 (m, 1H), 7.81 (d, J=8.7 Hz, 2H), 7.34 (d, J=8.8 Hz, 2H), 6.74 (d, J=10.7 Hz, 2H), 4.54 (dd, J=10.7, 8.9 Hz, 1H), 4.09-3.96 (m, 1H), 3.76 (s, 3H), 3.60-3.55 (m, 1H), 3.44-3.37 (m, 1H), 2.38 (s, 3H)

Example 64

$^1$H NMR (500 MHz, DMSO-$d_6$) δ 8.19-8.10 (m, 1H), 8.06 (q, J=8.1 Hz, 1H), 7.82 (d, J=8.8 Hz, 2H), 7.32 (d, J=8.8 Hz, 3H), 7.01 (dd, J=7.9, 1.3 Hz, 1H), 6.93 (dd, J=7.9, 2.3 Hz, 1H), 6.75 (d, J=10.7 Hz, 2H), 4.54 (dd, J=10.9, 8.9 Hz, 1H), 4.01 (q, J=9.6 Hz, 1H), 3.76 (s, 3H), 3.60-3.55 (m, 1H), 3.44-3.36 (m, 1H)

Example 65

$^1$H NMR (500 MHz, DMSO-$d_6$) δ 8.26-8.18 (m, 1H), 8.15-8.09 (m, 1H), 7.89-7.83 (m, 1H), 7.79 (d, J=8.8 Hz, 2H), 7.30-7.23 (m, 2H), 7.19 (dd, J=9.0, 3.6 Hz, 1H), 6.75 (d, J=10.7 Hz, 2H), 4.56-4.50 (m, 1H), 4.06-3.96 (m, 1H), 3.77 (s, 3H), 3.59-3.51 (m, 1H), 3.39 (m, 1H).

Example 66

$^1$H NMR (500 MHz, DMSO-$d_6$) δ 8.47-8.39 (m, 2H), 8.25 (s, 1H), 7.85 (d, J=8.5 Hz, 2H), 7.45-7.41 (m, 2H), 7.39-7.30 (m, 1H), 6.77 (d, J=10.7 Hz, 2H), 4.60-4.48 (m, 1H), 4.05-3.95 (m, 1H), 3.77-3.71 (m, 3H), 3.59-3.49 (m, 1H), 3.44-3.35 (m, 1H).

Example 67

$^1$H NMR (500 MHz, DMSO-$d_6$) δ 8.18-8.07 (m, 1H), 7.80 (d, J=8.3 Hz, 3H), 7.30 (d, J=8.7 Hz, 2H), 6.75 (d, J=10.8 Hz, 2H), 6.60 (dd, J=7.9, 3.4 Hz, 2H), 4.58-4.45 (m, 1H), 4.05-3.96 (m, 1H), 3.76 (s, 3H), 3.70 (s, 3H), 3.59-3.52 (m, 1H), 3.44-3.36 (m, 1H).

Example 68

$^1$H NMR (500 MHz, DMSO-$d_6$) δ 8.27-8.23 (m, 1H), 8.20-8.14 (m, 1H), 7.81 (d, J=8.5 Hz, 2H), 7.35-7.28 (m, 4H), 6.78 (d, J=10.7 Hz, 2H), 4.58-4.50 (m, 1H), 4.07-3.95 (m, 1H), 3.75 (s, 3H), 3.60-3.49 (m, 1H), 3.44-3.33 (m, 1H).

The invention claimed is:
1. A compound of formula I

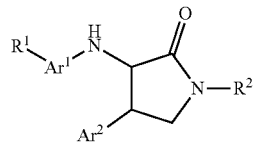

where:
$R^1$ is absent, $Ar^3$, cycloalkyl substituted with 0-2 halo and 0-1 $Ar^4$ substituents, or (($Ar^5$)alkyl)(H)NCO;
$R^2$ is hydrogen, alkyl, or $CH_2CO_2H$;
$Ar^1$ is isoxazolyl, oxadiazolyl, thiadiazolyl, benzoisoxazolyl, isoxazolopyridinyl, or benzooxazolyl, and is substituted with 0-2 halo, alkyl, alkoxy, fluoroalkyl, or fluoroalkoxy substituents;
$Ar^2$ is phenyl, pyridinyl, or pyridazinyl, and is substituted with 1 alkoxy, halo, haloalkyl or haloalkoxy substituent in the 4-position and 0-2 additional halo substituents;
$Ar^3$ is phenyl, pyridinyl, pyridazinyl, pyrimidinyl, or pyrazinyl, and is substituted with 0-3 substituents selected from cyano, halo, alkyl, haloalkyl, cycloalkyl, alkoxy, (cycloalkyl)alkoxy, haloalkoxy, $OAr^6$, alkylthio, haloalkylthio, alkylsulfinyl, haloalkylsulfinyl, and pyrazolyl;
$Ar^4$ is phenyl or pyridinyl substituted with 0-3 substituents selected from cyano, halo, alkyl, haloalkyl, alkoxy, and haloalkoxy;

Ar$^5$ is phenyl or pyridinyl substituted with 0-3 substituents selected from cyano, halo, alkyl, haloalkyl, alkoxy, and haloalkoxy; and Ar$^6$ is phenyl, pyridinyl, pyridazinyl, pyrimidinyl, or pyrazinyl, and is substituted with 0-3 substituents selected from cyano, halo, alkyl, haloalkyl, alkoxy, and haloalkoxy;

Provided when Ar$^1$ is oxadiazolyl or thiadiazolyl, Ar$^1$ is substituted with 0-1 halo, alkyl, alkoxy, fluoroalkyl, or fluoroalkoxy substituent;

or a pharmaceutically acceptable salt thereof.

2. A compound of claim 1 where R$^1$ is Ar$^3$; R$^2$ is hydrogen; Ar$^1$ is oxadiazolyl or thiadiazolyl, and is substituted with 0-1 halo, alkyl, alkoxy, fluoroalkyl, or fluoroalkoxy substituent; Ar$^2$ is phenyl substituted with 1 alkoxy, halo, haloalkyl or haloalkoxy substituent in the 4-position and 0-2 additional halo substituents; Ar$^3$ is phenyl or pyridinyl and is substituted with 0-3 substituents selected from cyano, halo, alkyl, haloalkyl, cycloalkyl, alkoxy, (cycloalkyl)alkoxy, haloalkoxy, OAr$^6$, alkylthio, haloalkylthio, alkylsulfinyl, haloalkylsulfinyl, and pyrazolyl; and Ar$^6$ is phenyl, pyridinyl, pyridazinyl, pyrimidinyl, or pyrazinyl, and is substituted with 0-3 substituents selected from cyano, halo, alkyl, haloalkyl, alkoxy, and haloalkoxy; or a pharmaceutically acceptable salt thereof.

3. A compound of claim 1 where R$^1$ is Ar$^3$.

4. A compound of claim 1 where R$^2$ is hydrogen.

5. A compound of claim 1 where Ar$^1$ is oxadiazolyl or thiadiazolyl, and is substituted with 0-1 halo, alkyl, alkoxy, fluoroalkyl, or fluoroalkoxy substituent; Ar$^2$ is phenyl substituted with 1 alkoxy substituent in the 4-position and 0-2 additional halo substituents.

6. A compound of claim 1 where Ar$^3$ is phenyl or pyridinyl and is substituted with 0-3 substituents selected from cyano, halo, alkyl, haloalkyl, cycloalkyl, alkoxy, (cycloalkyl)alkoxy, haloalkoxy, OAr$^6$, alkylthio, haloalkylthio, alkylsulfinyl, haloalkylsulfinyl, and pyrazolyl.

7. A composition comprising a compound of claim 1, or a pharmaceutically acceptable salt thereof, and a pharmaceutically acceptable carrier, diluent, or excipient.

* * * * *